(12) United States Patent
Das et al.

(10) Patent No.: US 9,642,854 B2
(45) Date of Patent: May 9, 2017

(54) FLAVANOID COMPOUNDS AND PROCESS FOR PREPARATION THEREOF

(71) Applicant: Council of Scientific & Industrial Research, New Delhi (IN)

(72) Inventors: Pratap Kumar Das, Kolkata (IN); Suchandra Goswami, Kolkata (IN); Annalakshmi Chinniah, Kolkata (IN); Janaswamy Madhusudana Rao, Kolkata (IN); Suresh Babu Katragadda, Kolkata (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/634,665

(22) Filed: Feb. 27, 2015

(65) Prior Publication Data

US 2015/0174135 A1     Jun. 25, 2015

Related U.S. Application Data

(62) Division of application No. 13/203,702, filed as application No. PCT/IN2010/000117 on Feb. 26, 2010, now Pat. No. 8,969,384.

(30) Foreign Application Priority Data

Feb. 27, 2009  (IN) .............................. 381/DEL/2009

(51) Int. Cl.
| | |
|---|---|
| *A61K 31/453* | (2006.01) |
| *A61K 31/496* | (2006.01) |
| *A61K 31/5377* | (2006.01) |
| *C07D 311/30* | (2006.01) |

(52) U.S. Cl.
CPC ........ *A61K 31/5377* (2013.01); *A61K 31/453* (2013.01); *A61K 31/496* (2013.01); *C07D 311/30* (2013.01)

(58) Field of Classification Search
None
See application file for complete search history.

(56) References Cited

FOREIGN PATENT DOCUMENTS

| WO | WO 2005/011671 A1 | 10/2005 |
|---|---|---|
| WO | WO 2007/080484 A2 | 7/2007 |

OTHER PUBLICATIONS

"Treatment." (2009).In Mosby's Dictionary of Medicine, Nursing, & Health Professions; Retrieved from <http://www.credoreference.com/entry/ehsmosbymed/treatment> on Nov. 18, 2010.
Aebischer et al.: "*Helicobacter pylori vaccine development: facing the challenge*";. Int. J. Med. Microbiol. 295(5), (2005), abstract.
Suresh, Babu K. et al.: "*Synthesis and Biological Evaluation of Novel C (7) Modified Chrysin Analogues as Antibacterial Agents*," Bioorg. Med. Chem. Lett. (2006), 16:221-224.

*Primary Examiner* — Alicia L Otton
(74) *Attorney, Agent, or Firm* — DLA Piper LLP (US)

(57) ABSTRACT

The present invention relates to flavanoid compounds of general formula ($X_1$) wherein: $R_1$ is selected from a group consisting of morpholinyl, N-methyl piperizinyl, piperidinyl and N,N'-dimethylamino groups, and n ranges from 3 to 6, and process for preparation thereof. The present invention relates to the demonstration of anti *Helicobacter pylori* activity and gastric antisecretory activity of semisynthetically designed flavonoid compounds, to be used for the prevention and treatment of gastroduodenal disorders in general and peptic ulcer diseases in particular. The present invention also relates to a hetero-dimeric bi-functional molecule that can be used as monotherapy substituting/replacing/overcoming currently used triple/quadruple therapy, thereby implicating/anticipating/envisaging its commercial applicability.

4 Claims, 6 Drawing Sheets

FLAVANOID COMPOUNDS AND PROCESS FOR PREPARATION THEREOF

CROSS-REFERENCE TO RELATED APPLICATIONS

Figure 1A:
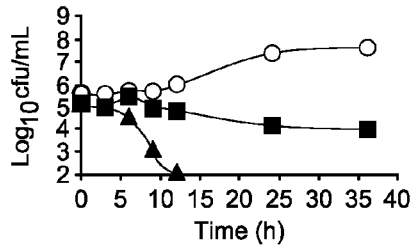
Figure 1F:
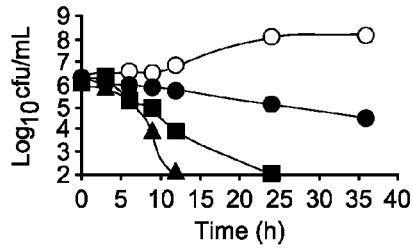
Figure 1B:
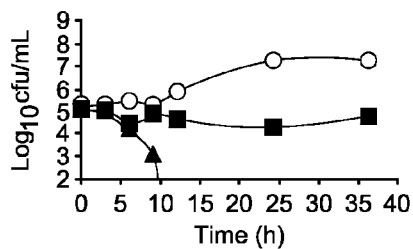
Figure 1G:
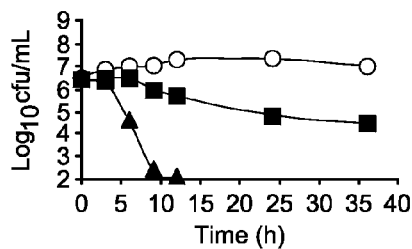
Figure 1C:
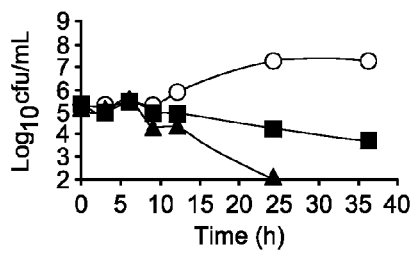
Figure 1H:
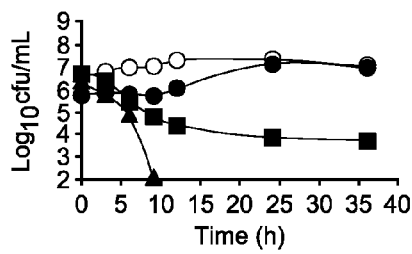
Figure 1D:
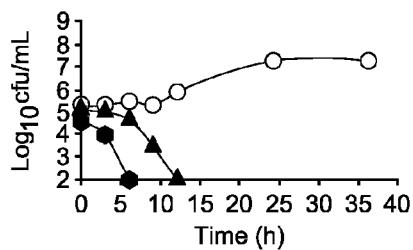
Figure 1I:
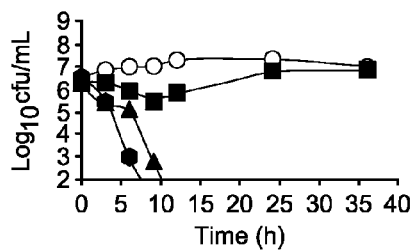
Figure 1E:
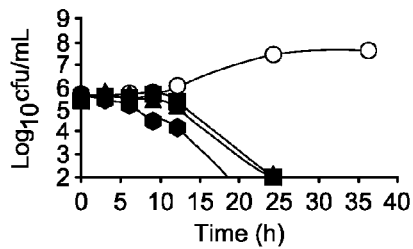
Figure 1J:
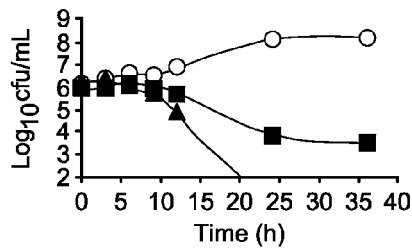

This application is a divisional application of U.S. application Ser. No. 13/203,702 filed Aug. 26, 2011, now issued as U.S. Pat. No. 8,969,384; which is a 35 USC §371 National Stage application of International Application No. PCT/IN2010/000117 filed Feb. 26, 2010; which claims the benefit under 35 USC §119(a) to India Patent Application No. 381/DEL/2009 filed Feb. 27, 2009.

BACKGROUND OF THE INVENTION

Field of the Invention

The present invention relates to flavonoid compounds and a process for preparation thereof. The present invention relates to the demonstration of anti *Helicobacter pylori* activity and gastric antisecretory activity of a semisynthetically designed flavonoid compounds, to be used for the prevention and treatment of gastroduodenal disorders in general and peptic ulcer diseases in particular.

Background Information

The aetiopathology of peptic ulcer disease is best understood in terms of an imbalance between mucosal defense factors (bicarbonate, mucin, prostaglandin, nitric oxide, some peptides and growth factors) and aggressive factors (acid, pepsin and *H. pylori*). Peptic ulcers do not occur when there is a balance between the aggressive factors and the defensive factors, but when the attacking factors become stronger than normal or when the defensive factors weaken, peptic ulcers can occur (Hoogerwerf and Pasricha, 2001).

*Helicobacter pylori* (*H. pylori*) is a ubiquitous, gram negative, highly motile, S-shaped, microaerophilic bacterium which colonizes the human gastric mucosa for extended time period. *H. pylori* infection is widespread with seroprevalence in the developed world between 30-60% (Everhart, 2000). Infection with the bacterium is usually contracted during childhood and patients remain infected for life unless treated. *H. pylori* infection has been shown to result in the development of chronic gastritis, gastro esophageal reflux disorder (GERD), and peptic ulcer diseases including gastric and duodenal ulcers. It is also linked to mucosa-associated lymphoid tissue (MALT) lymphoma, and gastric adenocarcinoma (Go, 2000).

The other major etiology of peptic ulcer diseases is hyperacid secretion. For ulcers that are not caused by *H. pylori*, acid suppressive therapy alone with antisecretory agents is recommended in the form of $H_2$-receptor antagonists or proton pump inhibitors, besides simple use of acid-neutralizing agents like antacids (Hoogerwerf and Pasricha, 2001). reflux The eradication of the bacterium by triple therapies consisting of two antibiotics and a proton pump inhibitor in infected patients has resulted in good healing rates for both active gastritis and peptic ulcer diseases (Graham et. al., 1992). However, rising prevalence of acquired resistance of *H. pylori* to some antibiotics (Glupczynski et al., 2001), ulcer recurrence and the relatively high incidence of side effects (Wermeille et al., 2002) are the major causes for concern in recent times. Strains resistant to clarithromycin (CLR) and metronidazole (MNZ) have been well documented (Mégraud, 2004) while resistance to amoxicillin (AMX) and tetracycline was mainly reported in Asian countries (Wu et al., 2000, Kwon et al., 2000). On the other hand, as far as the use of antisecretory agents $H_2$ receptor blockers and proton pump inhibitors are concerned, a number of side effects are reported. The adverse drug interaction of the cytochrome P450 system with H2-receptor blocker, hypersensitivity and damage of the liver by proton pump inhibitors, requirements of multiple doses of antacids to alleviate symptomatic-only relief, coupled with ulcer recurrence problems (Bullard, 1997) necessitate searching for better therapeutic management of hypersecretory disorders.

Regarding the treatment of *H. pylori* infection, reference may be made to an U.S. patent (Borody, 1993) which described a method consisting of the administration of a bismuth compound, an antibiotic belonging to the groups of penicillin and tetracycline, and a second antibiotic, such as metronidazole. The relevant therapy thus consists of the administration of three medications several times a day. There are other patents describing multiple therapies for the eradication of *H. pylori*, such as Neeman et al., 1995, 1996; Shell, 1996). None of these however eliminate the need to administer complex medications.

As antisecretory agents, several patents disclose the use of diverse molecular structures like fumagillol (Yanai et al. 1998), diphenyl ether phosphate esters (Catrenich et al., 1995), heterocyclyl-phenyl-(sulfonyl- or phosphonyl)-amidines (Cereda et al., 1987), N-alkylated benzo- and heterofused compounds (Schiehser et al., 1986), N-aryl-N'-(1,4,5, 6-tetrahydropyrimidin-2-yl)ureas (Ramussen, 1984), 4,5,6, 7-tetrahydroimidazo-[4,5-c]-pyridine (Arcari et al., 1980), 1-(4-chlorophenyl)-3-(1-ureido)-2-imidazolidinone (Schwan et al., 1978), 1,3-dimethyl-1H-pyrazolo(4,3-d)pyrimidine-7(6H)-ones (Ratajczyk et al., 1976), 4-acetoxy-1, 2,3,4-tetrahydro-2,2-dimethyl-6,7-methylenedioxy isoquinolinium iodide (Schwan et al., 1978), furan or thiophene derivatives of iminomethyl piperidine (Scott, 1986), and O-(carboxymethyl)-4-chromanone oxime (Wright et al., 1978).

Flavonoids, a class of polyphenols compounds, are present in many fruits and vegetables and offer a large number of biological activities. The antimicrobial activity of different types of flavonoids, either isolated from different plants or their chemically modified analogues, have been reported (Cushnie and Lamb, 2005). Anti peptic ulcer activity including anti *H. pylori* activity of naturally occurring flavonoids have also been documented (Beil et al., 1995; Ohsaki et al., 1999; Fukai et al., 2002; Park et al., 2004).

Three U.S. patents have disclosed the use of flavone or flavanone compounds for preventing or treating damages to the mucosal lining of the gastrointestinal tract (Ares et al., 1995; Yoo et al., 2000; Xu, 2004) while a Chinese patent (CN1615947) has implicated the use of flavones for treating oral ulcer, gastric ulcer, burn, scald and traumatic infection. A recent patent application from our group has disclosed the use of flavonoids for the treatment of gastrointestinal toxicity, associated symptoms and ulcers (Rao et al., 2007).

A Japanese patent (JP11228407) and an U.S. patent (Higuchi et al., 2001) disclosed the use of flavones for increasing the activity of beta lactam antibiotics against methicillin-resistant *Staphylococcus aureus*. An U.S. patent disclosed the use of biflavonoids in treating viral infection (Lin et al., 2002), while another U.S. patent disclosed the use of 3-methylene flavanones and 3-methylene chromanones having activity against microorganisms (Buckler et al., 1980). The use of flavones as antibacterial agents exhibiting suppressing effect against indigenous dermatic bacteria has been disclosed in the patent JP62145017. The antibacterial activity of an antibiotic flavone has also been disclosed in an US patent (Richards et al., 1972). Use of chrysin as antibacterial, antiviral and immunostimulatory agents has been patented (Markonius, 1995, 1999). Use of oroxylin A as inducible nitric oxide synthase inhibitor, cyclooxygenase-2 inhibitor and potassium channel activator has also been patented (Lee et al., 2004).

In view of the efforts towards searching for flavonoids which could be active against antibiotic-resistant bacterial strains or which would not impart resistance to otherwise susceptible strains (Xu and Lee, 2001; Iinuma et al., 1994; Liu et al., 2001), the inventors were interested in designing, synthesizing and bioevaluating a series of chrysin and oroxylin A derivatives with a view to imparting both anti H. pylori as well as antisecretory property in the flavone core structure.

Definition of the Abrreviations

ATP Adenosine triphosphate
AMX Amoxicillin
ATCC® American Type Culture Collection
BHI Brain Heart Infusion
CLSI® Clinical and Laboratory Standard Institute
CFU Colony Forming Unit
CMD Cimetidine
CLR Clarithromycin
DENT® A trademark product of Becton-Dickinson (antibiotic mixture)
DMSO Dimethyl sulfoxide
DCM Dichloromethane
DMF Dimethylformamide
EDC1 1-Ethyl-3-(3-dimethylaminopropyl) carbodimide
FCS Feotal Calf Serum
GERD Gastro esophagus reflux disorders
HOBt N-Hydroxybenzo triazole
$IC_{50}$ value 50% inhibitory concentration
MIC Minimum inhibitory concentration
MBC Minimum bactericidal concentration
MIC range Covering MIC values against a panel of H pylori, including standard strains and clinical isolates
$MIC_{50}$ value MIC values against 50% of the strain
MALT Mucosa-associated lymphoid tissue
MNZ Metronidazole
OPZL Omeprazole
PIPES-Tris piperazine-N,N'-(2-ethane sulfonic acid) Tris salt
PC Parietal cell
TCA Trichloroacetic acid

Objective of the Invention

The main objective of the present invention is to provide novel flavonoid compounds and process for preparation thereof.

Another objective of the present invention is to develop compounds, which could be therapeutically safe and useful in treating peptic ulcer diseases.

Another objective of the present invention is to design and develop such single compound(s) that should possess both anti H. pylori activity as well as gastric antisecretory activity so as to mitigate the two major aetiopathologies of peptic ulcer diseases, namely, the bug and the acid, thereby reducing the requirement of triple/quadruple therapy currently in practice.

Yet another objective of the present invention is to impart H. pylori inhibiting property and also gastric antisecretory property to a class of semi-synthetic flavonoids by structural modification of the side chain of the natural compounds chrysin and oroxylin A, along with simultaneously increasing the lipophilicity of the molecule, and by linking with another natural product molecule.

Still another objective of the present invention is to provide detailed experimental evidence for anti H. pylori activity and gastric antisecretory activity in one designed molecule 5-hydroxy-2-phenyl-7-(6-piperidin-1-yl-hexyloxy)-4H-benzpyran-4-one or, 5-hydroxy-2-phenyl-7-(6-piperidin-1-yl-hexyloxy)-chromen-4-one or in short, 7-O-(6-piperidin-1-ylhexyl)-chrysin (abbreviated in this document as CPP-1).

SUMMARY OF THE INVENTION

Accordingly, the present invention provides a flavonoid compound of general formula-$X_1$, wherein $R_1$ is selected from a group consisting of morpholinyl, N-methyl piperizinyl, piperidinyl and N,N'-dimethylamino groups, and value of n is 3-6, or a pharmaceutically acceptable salt thereof.

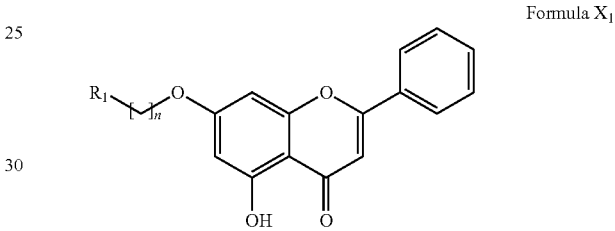

Formula $X_1$

In an embodiment of the present invention, the structure of representative compounds of

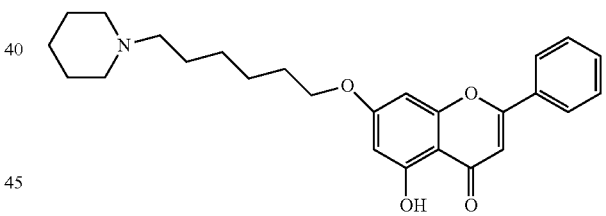

CPP-1

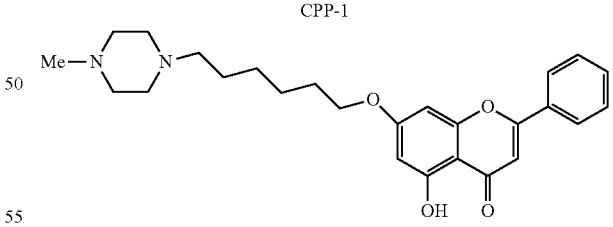

NMG-1

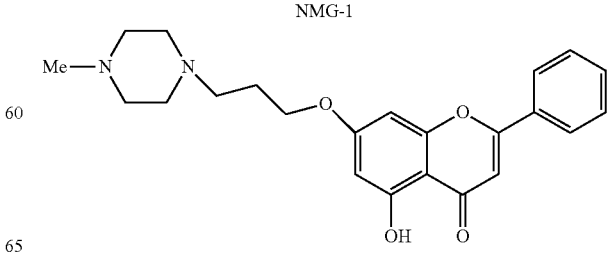

NMG-2

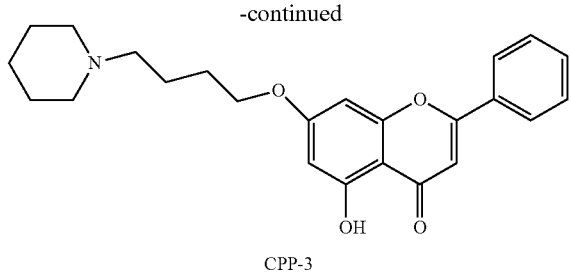

CPP-3

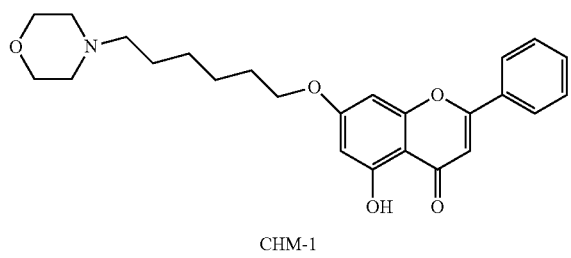

CHM-1

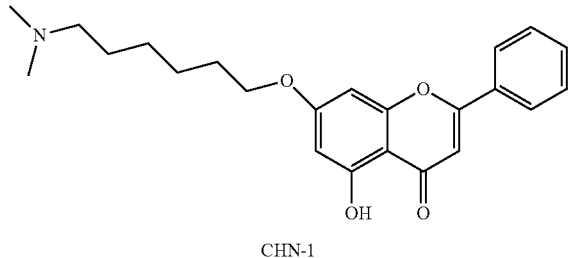

CHN-1 general formula $X_1$ comprising:

In an embodiment of the present invention the representative compounds comprising:
 (a) 5-Hydroxy-2-phenyl-7-(6-piperidin-1-yl-hexyloxy)-chromen-4-one (CPP-1)
 (b) 5-Hydroxy-7-[6-(4-methyl-piperazin-1-yl)-hexyloxy]-2-phenyl-chromen-4-one (NMC-1)
 (c) 5-Hydroxy-7-[3-(4-methyl-piperazin-1-yl)-propoxy]-2-phenyl-chromen-4-one (NMC-2)
 (d) 5-Hydroxy-2-phenyl-7-(4-piperidin-1-yl-butoxy)-chromen-4-one (CPP-3)

In an embodiment of the present invention, the pharmaceutically acceptable salt is any addition salt of an acid selected from chloride, sulphate, maleate, tartrate, phosphate and acetate.

In an embodiment of the present invention, the compounds are useful as potential anti *Helicobacter pylori* as well as gastric antisecretory agent which could be a monotherapy drug candidate for prevention and treatment of peptic ulcer diseases.

In still another embodiment of the present invention, said compounds show bacteriostatic as well as bactericidal activity against clinical as well as ATCC® standard strains of *H. pylori*.

In an embodiment of the present invention, said compounds are equally effective at acidic pH, the gastric lumen environmental pH where these are supposed to act.

In an embodiment of the present invention, said compounds do not develop resistance to several subcultures of *H. pylori*, in clinical strain or with standard strain upon long term use.

In an embodiment of the present invention, 5-hydroxy-2-phenyl-7-(6-piperidin-1-yl-hexyloxy)-4H-benzpyran-4-one (CPP-1), has been demonstrated to induct irreversible morphological deformation of *H. pylori* at its MIC/MBC dose range of 6.25-12.5 µg/mL, effectively kill the bacteria at pH ranging from 4-6 unlike clarithromycin, and remain potentially active towards the bacteria upon repeated exposure unlike metronidazole.

In an embodiment of the present invention, said compound, 5-hydroxy-2-phenyl-7-(6-piperidin-1-yl-hexyloxy)-4H-benzpyran-4-one (CPP-1), inhibits gastric $H^+$ pump activity with an $IC_{50}$ value of 10 (±2) µg/mL.

In an embodiment of the present invention, 5-hydroxy-2-phenyl-7-(6-piperidin-1-yl-hexyloxy)-4H-benzpyran-4-one (CPP-1), inhibits acid hypersecretion in gastric parietal cells.

In an embodiment of the present invention, 5-hydroxy-2-phenyl-7-(6-piperidin-1-yl-hexyloxy)-4H-benzpyran-4-one (CPP-1), inhibits basal acid secretion in gastric parietal cells in a dose-dependent manner with $IC^{50}$ value of 5 (±1) µg/mL.

In an embodiment of the present invention, 5-hydroxy-2-phenyl-7-(6-piperidin-1-yl-hexyloxy)-4H-benzpyran-4-one (CPP-1), inhibits histamine-stimulated acid secretion in gastric parietal cells in a dose-dependent manner with $IC_{50}$ value of 15 (±3) µg/mL.

Accordingly the present invention provides a process for preparation of compounds of general formula $X_1$, wherein the process steps comprising:

(a) reacting chrysin of formula I with 1,n-dibromoalkane (n=3 to 6) in presence of a base selected from the group consisting of potassium carbonate, sodium carbonate and cesium carbonate in a solvent selected from acetone and acetonitrile under nitrogen atmosphere to afford 7-O-(n-bromoalkyl)chrysin of formula (III),

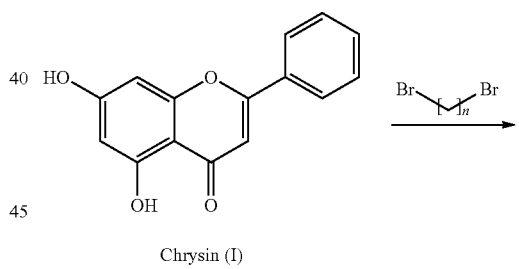

Chrysin (I)

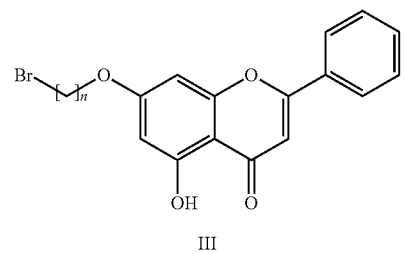

III (b) reacting the compound (III) with an amine selected from a group consisting of morpholine, N-methyl piperazine, piperidine, N,N'-dimethyl amine in presence of a base selected from the group consisting of potassium carbonate, sodium carbonate and cesium carbonate in a solvent selected from anhydrous acetonitrile and acetone under nitrogen atmosphere to afford the desired compounds of formula $X_1$

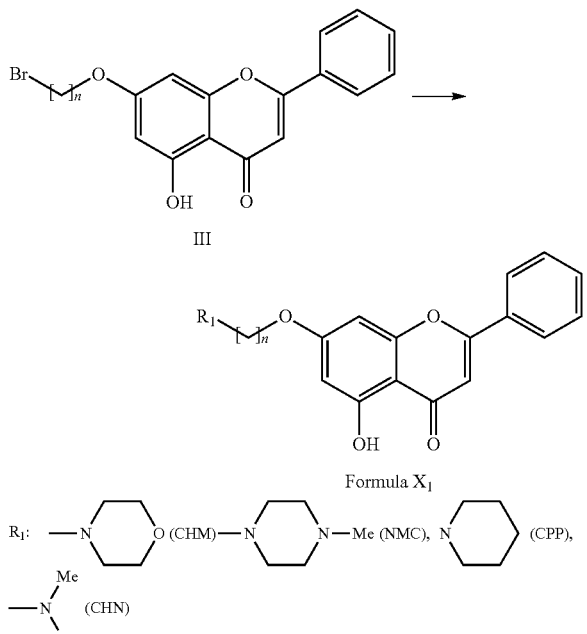

n = 3 indicates 2-series like CHM-2, NMC-2, CPP-2, CHN-2
n = 4 indicates 3-series like CHM-3, NMC-3, CPP-3, CHN-3
n = 6 indicates 1-series like CHM-1, NMC-1, CPP-1, CHN-1

Present invention also provides a pharmaceutical composition for treating or preventing *H. pylori* infection and gastric hypersecretion in a subject comprising a pharmaceutically effective amount of the compound of formula $X_1$ optionally along with one or more pharmaceutically acceptable carriers, additives, lubricants and diluents, wherein the ratio of the compound of general formula $X_1$ to the additives ranging from 1-10: 10-1.

In an embodiment of the present invention, the carriers used are selected from the group consisting of proteins, carbohydrates, sugar, magnesium stearate, cellulose, calcium carbonate, starch-gelatin paste and pharmaceutically acceptable excipients, diluents or solvents.

In an embodiment of the present invention, the composition to be administered in human at a dose ranging between 20-60 mg twice per day.

In an embodiment of the present invention, the composition is useful for treating or preventing *H. pylori* infection and gastric hypersecretion leading to management of peptic ulcer diseases, which include one or more of the following disorders: gastric peptic ulcer, duodenal peptic ulcer, chronic and acute gastritis, chronic and acute duodenitis, non-ulcer dyspepsia, gastro esophageal reflux disorders, mucosa-associated lymphoid tissue lymphoma and gastric adenocarcinoma.

The present invention deals with the development of a designed molecule, 5-hydroxy-2-phenyl-7-(6-piperidin-1-yl-hexyloxy)-4H-benzpyran-4-one, that effectively kills the bacterium *Helicobacter* pylori as well as inhibits gastric hypersecretion, giving rise to an unique single compound therapy for the management of peptic ulcer diseases.

BRIEF DESCRIPTION OF THE TABLES AND DRAWINGS

Table 1a exhibits representative compounds of 7-O-alkylamino derivative of chrysin (Formula $X^1$).

Table 1b shows representative compounds of 7-O-acyl derivative of oroxylin A (Formula $X^2$).

The IUPAC name was obtained using AutoNom 1.0 add-in for ISIS draw from MDL Information Systems, Inc.

Table 2 shows anti *H. pylori* activity of the compound analogues.

The discs were impregnated with 100 and 200 mg of each of the compounds, dissolved either in ethanol or DMSO, and the zone of inhibition was measured after 72 h of growth under microaerophilic conditions at 37° C. Inhibition zone diameter ranging 10-20 mm was given a score of +, 20-30 mm as ++ and that of >30 mm as +++, as obtained employing dose range of 100 and 200 mg/disc. The detailed structural information of the molecules is provided under 'Description of the Compounds'.

Table 3 shows anti *H. pylori* spectrum of the compounds, and Table 3a summarizes MIC range and $MIC_{50}$ values of such compounds.

MIC was determined using agar dilution assay following the CLSI® guidelines. Six clinical isolates and four standard strains were used for this study. Five microlitre of freshly grown 3-day old culture (~1×10$^8$ CFU/mL) was streaked in plates containing 2-fold serial dilution of the compounds ranging 1.56-100 mg/mL, and incubated under microaerophilic condition at 37° C. After 72 h, the plates were inspected visually for absence of growth to assess the MIC values. The experiment was performed in duplicates. $MIC_{50}$ is defined as the dose (µg/ml) required for killing 50% of the strains.

Table 4 exhibits MIC and MBC values of four most active compounds, determined by microbroth dilution method.

The compounds, serially diluted (3.125-100 mg/mL) in Muller Hinton broth containing 5% FCS, were incubated in 96-well microtitre plate containing fresh cultures of HP001 (~5.5×10$^6$ CFU/mL) or ATCC® 43504 (2.65×10$^6$ CFU/ml) in a final volume of 200 ml. After 72-h of incubation under microaerophilic condition at 37° C., 100 ml of cultures wherein no growth had been detected were streaked on fresh brain heart infusion agar plates for MBC determination.

Table 5 shows anti *H. pylori* activity evaluation of the spacer molecules by disc diffusion sensitivity assay and microbroth dilution assay.

Methods and protocols for the determination of inhibition zone diameter are as stated under Experiment 1, and that of MIC values by microbroth dilution assay as in Experiment 3. 'Nil' means zone of inhibition below 10 mm.

Table 6 exhibits acid stability study of CPP-1, NMC-1, NMC-2 and CPP-3.

Details of experimental protocol are described under Experiment 7. MIC/MBC values were determined by microbroth dilution assay.

Table 7 shows the effect of CPP-1 on pig gastric H$^+$K$^+$-ATPase activity.

The data are averages of 3-4 determinations each carried out in triplicate. The assay system contained 10 mM PIPES-Tris (pH 6.8), 2 mM each of ATP and $MgCl_2$ with or without 10 mM KCl and about 10 mg membrane protein in a final volume of 1 mL. Both blank and experimental tubes with or without CPP-1 at different concentrations were preincubated with otherwise complete assay mixture at 37° C. for 10 min before initiating the reaction with the substrate ATP. K$^+$-stimulated activity referred to as H$^+$,K$^+$-ATPase activity, was calculated as the difference between the activity in presence of Mg$^{2+}$ plus K$^+$ and the basal activity (Mg$^{2+}$-ATPase) in presence of Mg$^{2+}$ alone. The specific activity of H$^+$,K$^+$-ATPase in control sets was in the range of 40-50 µmole Pi/mg protein/h.

FIGS. 1A-1J represent time-kill analyses of compounds CPP-1, NMC-1, NMC-2 and CPP-3 against two *H. pylori* strains, clinical isolate HP001 and ATCC® 43504.

Left-side panels (FIGS. 1A-1E) HP001; right-side panels (FIGS. 1F-1J) ATCC® 43504. The time and dose-kill curves for each of the compounds represent, whenever applicable, 0.5XMIC (filled circles), 1XMIC (filled squares), 2XMIC (filled triangles) and 4XMIC (filled hexagons). Control (open circles), bacterial suspension without compound or antibiotic, contained either ethanol or DMSO at the concentration used. MICs of CPP-1 (FIGS. 1A and 1F) and NMC-1 (FIGS. 1B and 1G) and that of NMC-2 (FIGS. 1C and 1H) and CPP-3 (FIGS. 1D and 1I), against both the strains, were 6.25 and 12.5 µg/mL respectively. The MICs of clarithromycin against HP001 (panel e) and ATCC® 43504 (panel j) were 0.01 µg/mL and 0.04 m/mL respectively.

Figure 2A:
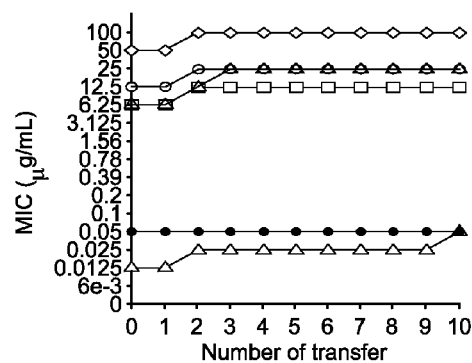
Figure 2B:
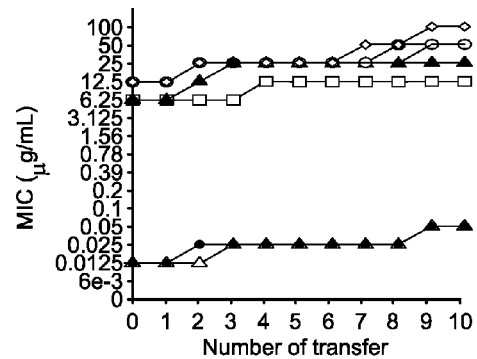

FIGS. 2A and 2B show an experiment that examined development of resistance to test compounds CPP-1, NMC-1, NMC-2, and NMC-3 and also clarithromycin, amoxicillin and metronidazole in ATCC® 43504 (FIG. 2A) and clinical strain HP001 (FIG. 2B).

Drugs were prepared as 2-fold dilutions in medium in 96-well microplates. The test strains were added with an inoculum size of approximately $10^6$ CFU/well. After 3-day incubation, the culture from each series with the highest concentration of the drugs and also showing turbidity was subcultured in a fresh series and as such the process was repeated ten times. MIC minimum inhibitory concentration; CLR—clarithromycin; AMX—amoxicillin; MNZ—metronidazole.

FIGS. 3A-1, 3A-2, 3A-3 and 3A-4 show time kill analysis of CPP-1 at respectively different pH values of 4.0, 5.0, 6.0 and 7.2.

The bacterial suspension (ATCC® 43504) was incubated in biphasic culture seeded with CPP-1 at different concentrations under microaerophilic atmosphere at 37° C. The samples were taken for viable count at 0, 3, 6, 9, 12 and 24 h. Symbols: ○ control; ● 6.25 mg/mL; ■ 12.5 mg/mL; ▲ 25 mg/mL.

FIGS. 3B-1, 3B-2, 3B-3 and 3B-4 show short-time kill, kinetics study of CPP-1 at respectively different acidic pH values of 4.0, 5.0, 6.0 and 7.2.

Employing ATCC® 43504 strain in shake culture, short time killing kinetics with the most potent molecule CPP-1 was investigated at pH 4.0, 5.0 and 6.0. Control (open circle); CPP-1 50 µg/mL (filled circle); CPP-1 100 µg/mL (filled square); CPP-1 150 µg/mL (filled triangle).

FIGS. 4A-4D show morphological transformation of HP001 upon 24-h exposure to increasing concentrations of CPP-1.

Figure 4A:
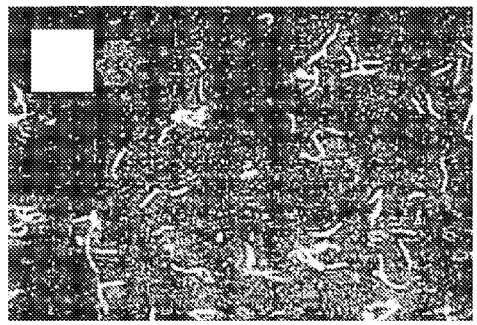
Figure 4B:
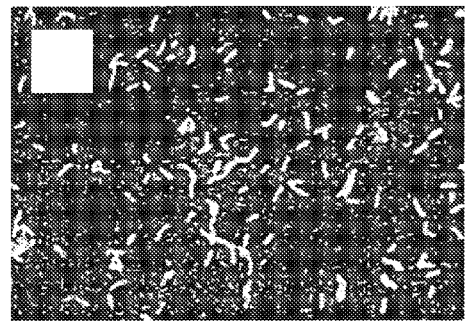
Figure 4C:
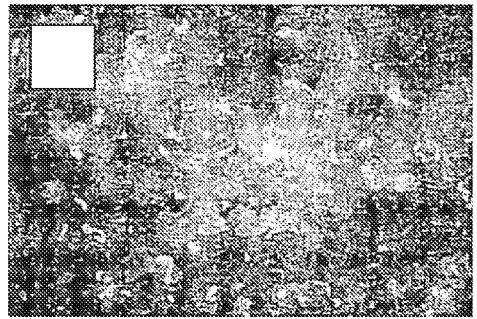
Figure 4D:
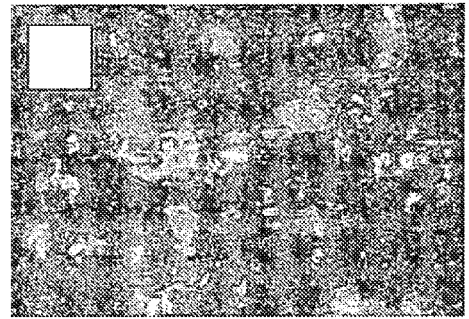

FIG. 4A: Control; FIG. 4B: 3.125 mg/mL CPP-1; FIG. 4C: 6.25 mg/mL CPP-1 and FIG. 4D: 12.5 mg/mL CPP-1. Acridine orange fluorescence microscopic evidence is provided. The details of experimental procedures are provided under Experiment 9.

FIGS. 5A-1, 5A-2, 5B-1, 5B-2, 5C-1 and 5C-2 show transmission electron micrograph of *H pylori* exposed to CPP-1.

Figures 1, 5A:
Figures 2, 5A:
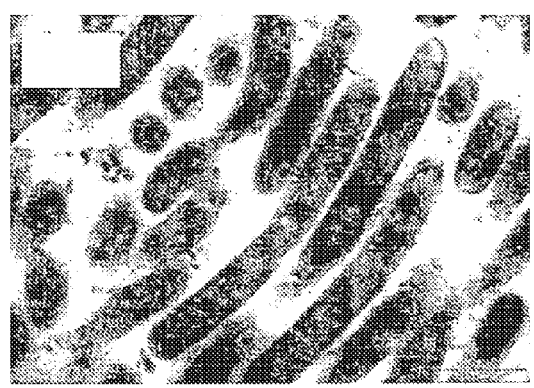
Figures 1, 5B:
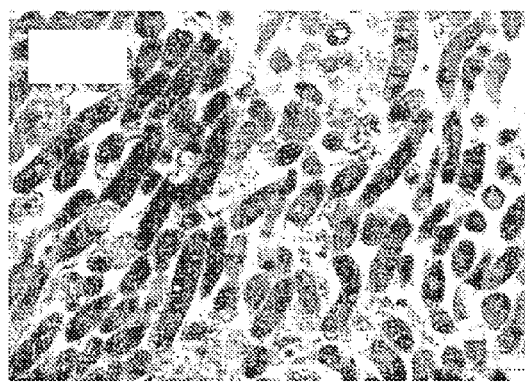
Figures 2, 5B:
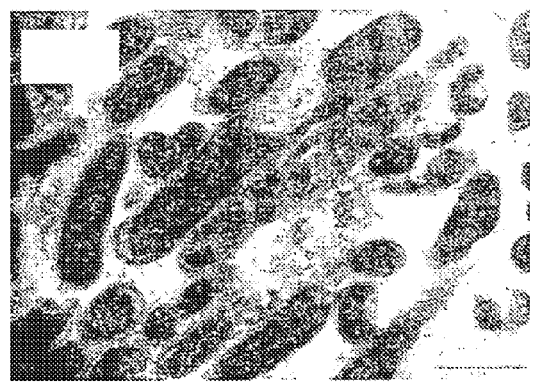
Figures 1, 5C:
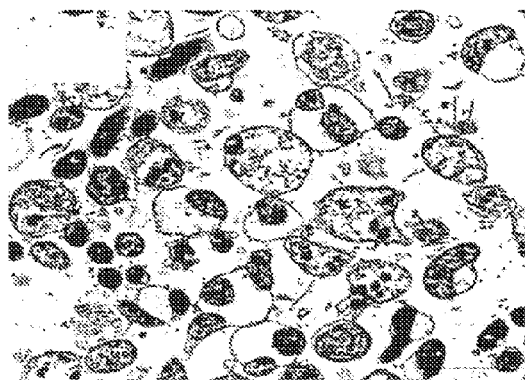
Figures 2, 5C:
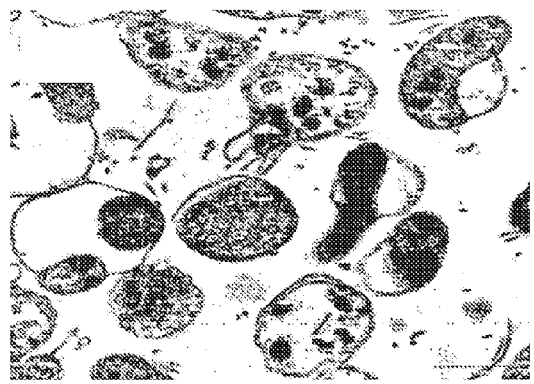

*H. pylori* ATCC® 43504 43504 cells were treated with CPP-1 for 24 h under microaerophilic condition at 37° C. in the absence (FIG. 5A-1), and the presence of 6.25 µg/mL (FIG. 5B-1) and 12.5 (µg/mL (FIG. 5C-1) of CPP-1. FIGS. 5A-1, 5B-1 and 5C-1 show 8,200× magnifications of the electron micrographs. FIGS. 5A-2, 5B-2 and 5C-2 depict higher magnifications (16,500×) of the correspondingly same micrographs depicted on the same row (FIG. 5A-2 control; FIG. 5B-2 6.25 µg/mL; and FIG. 5C-2 12.5 µg/mL).

Figure 6A:
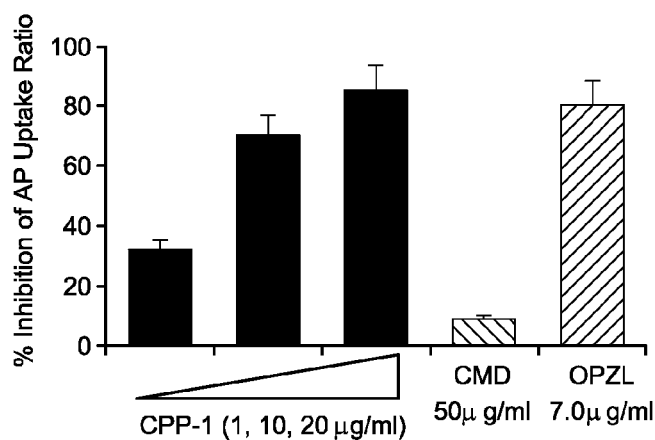

FIG. 6A demonstrates the effect of CPP-1 on basal acid secretion in gastric parietal cell. Dose-dependent inhibition of aminopyrine (AP) uptake ratio in parietal cell suspension after CPP-1 treatment was measured.

Figure 6B:
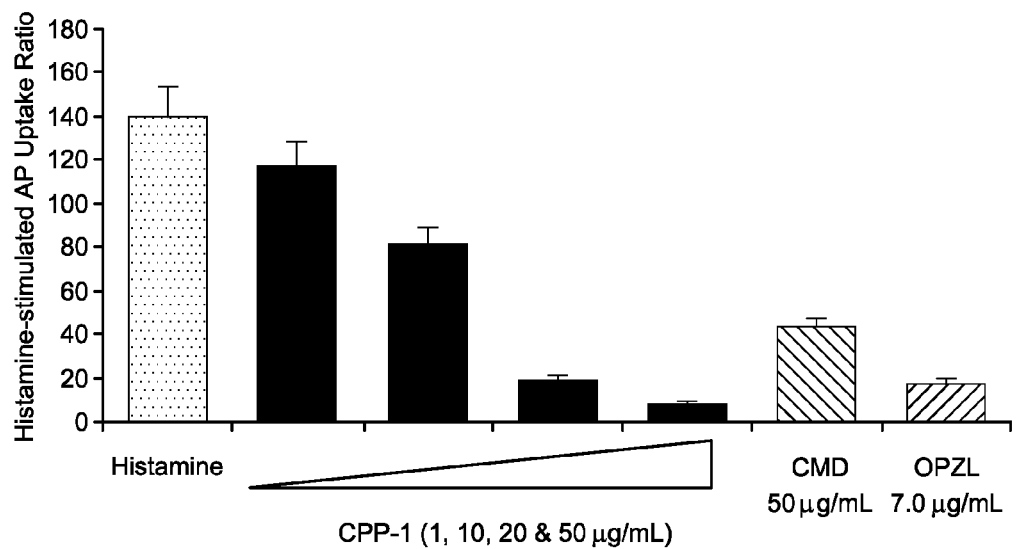

FIG. 6B shows the effect of CPP-1 on histamine-stimulated (0.1 mM) acid secretion in gastric parietal cell. Dose-dependent inhibition of histamine-stimulated aminopyrine (AP) uptake ratio in parietal cell suspension after CPP-1 treatment was measured.

CMD: cimetidine; OPZL: omeprazole. In all experiments, the data represent averages of 2-3 determinations each carried out in triplicate.

DETAILED DESCRIPTION OF THE INVENTION

The present invention relates to the development of a semi-synthetic hetero-dimer of chrysin and piperidine, clicked via $(CH_2)_n$ spacer linkage, namely CPP-1 and analogues thereof, as anti *H. pylori* as well as gastric antisecretory agent, which is being envisaged as a potential mono-therapy drug for the prevention and treatment of peptic ulcer diseases. Thus, the conferred bi-functional activity within a single molecule has been disclosed here for the development of novel antiulcer therapeutics.

It is to be borne in mind that the current world-wide therapeutic regimen is typically triple/quadruple therapy comprising of one or two antibiotics to kill the bacteria (like clarithromycin, amoxicillin and/or metronidazole, 1-2 antisecretory agent (either in the form of $H_2$ receptor blocker like ranitidine, famotidine etc or gastric proton pump inhibitor like omeprazole, rabeprazole, pantoprazole etc), occasionally with a mucus coating agent also like bismuth tricitrate. The present invention disclosed both the anti *H. pylori* and the antisecretory activity in one molecule. Thus, this invention has immense commercial implications besides being extremely novel in its approach.

In an effort to design molecules that could possess both anti *Helicobacter pylori* activity and also gastric antisecretory potential, to be used for the treatment of gastroduodenal ulcers, the inventors synthesized a series of semisynthetic flavonoids, examined for their anti *H. pylori* properties, picked up the best molecule, and finally demonstrated gastric antisecretory activity in such potent anti *H. pylori* compound. Two series of flavone analogues, 7-O-alkylamino derivatives of chrysin and 7-O-acyl derivatives of oroxylin A, and the parent chrysin and oroxylin A obtained from the medicinal plant *Oroxylum indicum*, were evaluated in vitro for anti *H. pylori* activity as a function of several necessary parameters, employing a panel of clinical isolates as well as standard strains. The most potent molecule 5-hydroxy-2-phenyl-7-(6-piperidin-1-yl-hexyloxy)-4H-benzpyran-4-one (CPP-1) showed MIC range of 3.125-25 µg/mL, $MIC_{50}$ of 3.125 µg/mL and MBC 6.25-12.5 µg/mL with demonstrated efficacy against drug-resistant as well as sensitive strains, could kill the bacteria within 12 h at 12.5 µg/mL doses, was functionally active at acidic pH unlike clarithromycin, and did not develop drug resistance unlike metronidazole. Neither the chrysin/oroxylin A core structure nor the spacer-linked n-alkylated amine ring system alone could contribute to the activity that such designed heterodimers manifest. The compound CPP-1 exhibited in vitro anti gastric $H^+,K^+$-ATPase activity with an $IC_{50}$ value of 10 µg/mL, demonstrated dose-dependent inhibition of basal acid secretion ($IC_{50}$ 5 µg/mL) as well as histamine-stimulated acid secretion ($IC_{50}$ 15 µg/mL) in rabbit gastric parietal cell, indicating thereby its potential as gastric antisecretory principle. The conferred bi-functional activity within a single molecule has been disclosed here for the development of newer antiulcer therapeutics.

For the development of newer therapeutic agents, the inventors investigated a wide range of Indian biodiversity including plant and microbial resources (Jayaraman, 2003). As a result, some of the plants and their parts were primarily considered as 'leads' for the development of anti peptic ulcer agent (Rao et al., 2007; Das et al, 2007a, b). *Oroxylum indicum* is one such medicinally important plant of Indian biodiversity that showed hints of anti ulcer activity in several preclinical experimental models (Khandhar et al., 2006). Most parts of the tree are used medicinally. The fresh root bark is a well known drug in Ayurvedic medicine as an ingredient of the compound formulation Dashamularishta "concoction of ten roots" (Jabbar et al., 2004). It is also reported that the powdered stem bark is given in dropsy and eruptive fevers, and the stem bark mixed with neem powder is used to treat fevers among tribal inhabitants of southern Bihar (Singh, 2002). Chrysin and oroxylin A are two naturally occurring flavones that are abundantly present in *O. indicum* (Ali et al., 1998; Babu et al., 2005, 2006).

Since these compounds are abundantly present in various plants, they can be obtained by extraction from plants. In particular, these compounds are present in the plant *Oroxylum indicum* belonging to the family Bignoniaceae, in a large amount and, therefore, they can be obtained easily by extraction from such plants. Alternatively, these compounds can also be prepared by synthesis.

The present invention relates generally to development of molecules for inhibiting the growth of pathogenic bacteria and gastroduodenal pathogenesis due to *Helicobacter* species, such as *H. pylori*. In a preferred embodiment, the methods and compositions are designed so as to substantially eradicate ulcer-causing bacteria. The term substantially eradicates preferably means at least 50%, more preferably 75%, and most preferably 95% of the *H. pylori* are killed.

The present invention additionally relates to the demonstration of anti gastric acid secretion property of one or more of such compounds as well as establishing the method of affecting gastric acid secretion and formulating pharmaceutical preparations containing one or more of the said compounds.

Description of the Compounds

The present invention provides a composition comprising of a compound having a chrysin moiety (5,7-dihydroxy-2 phenyl chromen-4-one) that is bridged to different varieties of heterocyclic ring system at 7 position, preferably N-methyl piperazine, piperidine, morpholine, or to dimethylamine, through an ether linkage, via 2-6 methylene spacers in between, or a pharmaceutically acceptable, non-toxic, acid-addition salt thereof in a therapeutically effective amount. The present invention also provides a composition comprising of a compound having 7-O-acyl derivatives of oroxylin A, or a pharmaceutically acceptable, non-toxic, acid-addition salt thereof in a therapeutically effective amount.

One embodiment of the present invention relates to anti *H. pylori* activity evaluation of a series of semisynthetic 7-O-alkylamino derivatives of chrysin (I), represented by the formula $X_1$ wherein $R_1$ is selected from morpholinyl, N-methyl piperizinyl, piperidinyl and N,N'-dimethylamino, and n is 3-6, or a pharmaceutically acceptable salt thereof.

In another embodiment, the present invention relates to anti *H. pylori* activity evaluation of 7-O-acyl derivatives of oroxylin A (II) represented by the formula $X_2$, wherein $R_2$ is selected from $C_{17}$ alkyl or 4-tolyl, or a pharmaceutically acceptable salts thereof.

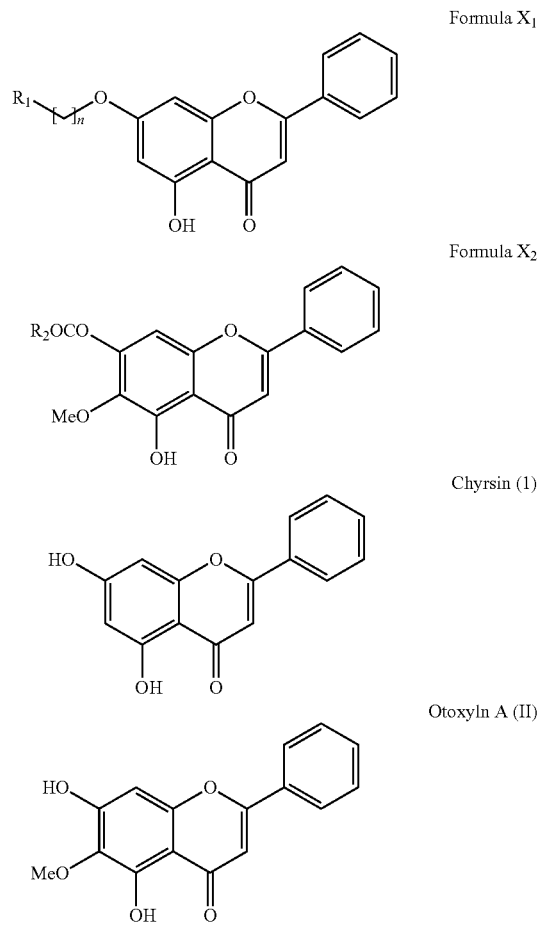

Representative compounds of Formula $X_1$ and Formula $X_2$ are described in Table 1a and 1b respectively below.

TABLE 1a

Representative compounds of 7-O-alkylamino derivative of chrysin (Formula $X_1$)

| Entry No. | $R_1$—(CH$_2$)$_n$ | Common name | Compound name (IUPAC)* |
|---|---|---|---|
| 1 | H | Chrysin | 5,7-Dihydroxy-2-phenyl-chromen-4-one |
| 1 | morpholine-(CH$_2$)$_6$ | CHM-1 | 5-Hydroxy-7-(6-morpholin-4-yl-hexyloxy)-2-phenyl-chromen-4-one |
| 2 | 4-methylpiperazine-(CH$_2$)$_6$ | NMC-1 | 5-Hydroxy-7-[6-(4-methyl-piperazin-1-yl)-hexyloxy]-2-phenyl-chromen-4-one |
| 3 | piperidine-(CH$_2$)$_6$ | CPP-1 | 5-Hydroxy-2-phenyl-7-(6-piperidin-1-yl-hexyloxy)-chromen-4-one |

TABLE 1a-continued

Representative compounds of 7-O-alkylamino derivative of chrysin (Formula $X_1$)

| Entry No. | $R_1$—$(CH_2)_n$ | Common name | Compound name (IUPAC)* |
|---|---|---|---|
| 4 | (structure) | CHN-1 | 7-(6-Dimethylamino-hexyloxy)-5-hydroxy-2-phenyl-chromen-4-one |
| 5 | (structure) | CHM-2 | 5-Hydroxy-7-(3-morpholin-4-yl-propoxy)-2-phenyl-chromen-4-one |
| 6 | (structure) | NMC-2 | 5-Hydroxy-7-[3-(4-methyl-piperazin-1-yl)-propoxy]-2-phenyl-chromen-4-one |
| 7 | (structure) | CPP-2 | 5-Hydroxy-2-phenyl-7-(3-piperidin-1-yl-propoxy)-chromen-4-one |
| 8 | (structure) | CHN-2 | 7-(3-Dimethylamino-propoxy)-5-hydroxy-2-phenyl-chromen-4-one |
| 9 | (structure) | CHM-3 | 5-Hydroxy-7-(4-morpholin-4-yl-butoxy)-2-phenyl-chromen-4-one |
| 10 | (structure) | NMC-3 | 5-Hydroxy-7-[4-(4-methyl-piperazin-1-yl)-butoxy]-2-phenyl-chromen-4-one |
| 11 | (structure) | CPP-3 | 5-Hydroxy-2-phenyl-7-(4-piperidin-1-yl-butoxy)-chromen-4-one |
| 12 | (structure) | CHN-3 | 7-(4-Dimethylamino-butoxy)-5-hydroxy-2-phenyl-chromen-4-one |

*The IUPAC name was obtained using AutoNom 1.0 add-in for ISIS draw from MDL Information Systems, Inc.

The methods of isolation and/or synthesis, and structural characterization of chrysin and oroxylin A and the synthetic analogues as in entry no. 5-14 (Tables 1a, 1b) are disclosed in patent application WO/2007/080484.

Method of Making a Few Designed Compounds of the Present Invention

In general, the compounds of this invention may be prepared by standard techniques known in the art, by known processes analogues thereto, and/or by the processes discussed below, using starting materials which are either naturally obtained, commercially available, producible according to routine, conventional chemical methods, and/or the synthesis of which are described herein (Babu et al., 2005, 2006; Rao et al., 2007).

However, based on the objectives of this invention and the observations disclosed in the earlier patent (Rao et al., 2007), we wanted to design synthesize such molecules that would impart both anti *H. pylori* activity and gastric antisecretory activity, so as to mechanistically mitigate the two major causes of peptic ulcer diseases (the bug *H. pylori* and the acid HCl), thereby effectively achieving the central objective of this invention that a single molecule can be designed which would replace the currently prevailing triple therapy.

Thus, the chromen-4-one derivatives of Formula $X_1$ where $R_1$ is morpholinyl, N-methyl piperizinyl, piperidinyl and N,N'-dimethylamino, can be prepared by the method outlined below in Scheme I and as described in Babu et al. (2006).

In Scheme I, the 7-O-hexyl chrysin derivatives of formula $X_1$ where $R_1$ is morpholinyl, N-methyl piperizinyl, piperidinyl and N,N'-dimethylamino may be synthesized by alkylation of chrysin (I) using 1,6 dibromo hexane in presence of a base such as potassium carbonate in a solvent such as acetone under reflux condition to afford 7-O-(6-bromo-hexyl)-chrysin (III). The appropriate amine (morpholine/N-methyl piperazine/piperidine/N,N'-dimethyl amine) was alkylated with compound (III) in presence of a base such as potassium carbonate in a solvent such as anhydrous acetonitrile under reflux condition to afford the desired compounds of 7-O-hexyl chrysin derivatives (CHM-1, NMC-1, CPP-1, CHN-1).

Scheme I

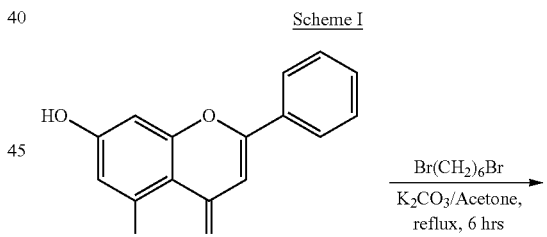

I $\xrightarrow{\text{Br(CH}_2)_6\text{Br}}_{\text{K}_2\text{CO}_3/\text{Acetone, reflux, 6 hrs}}$

TABLE 1b

Representative compounds of 7-O-acyl derivative of oroxylin A (Formula $X_2$)

| Example Entry. No. | $R_2$ | Common name | Compound name (IUPAC)* |
|---|---|---|---|
| 13 | (structure, 16) | ORC-16 | Heptadecanoic acid 5-hydroxy-6-methoxy-4-oxo-2-phenyl-4H-chromen-7-yl ester |
| 14 | (structure) | ORPM-1 | 4-methyl-benzoic acid 5-hydroxy-6-methoxy-4-oxo-2-phenyl-4-H-chromen-yl ester |

*The IUPAC name was obtained using AutoNom 1.0 add-in for ISIS draw from MDL Information Systems, Inc.

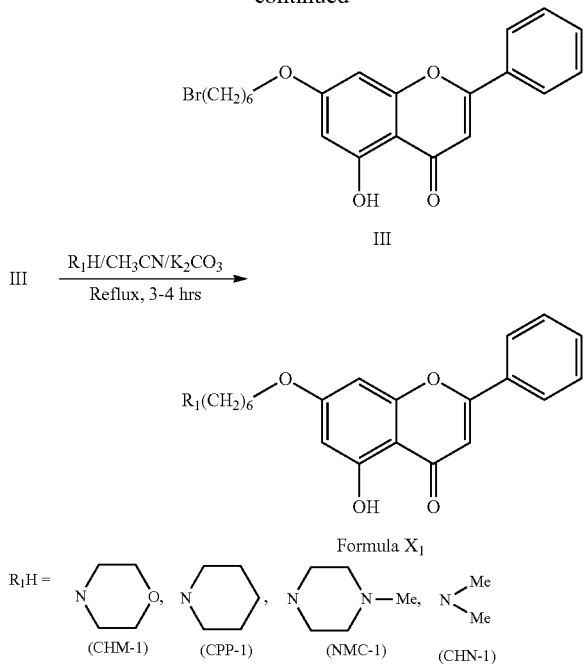

A compound of formula $X_2$ where $R_2$ is $C_{17}$ alkyl or 4-tolyl can generally be synthesized from oroxylin A (II) as described in Babu et al. (2005).

The following examples are given by way of illustration and should not construed the scope of the present invention.

EXAMPLE 1

Preparation of 5-hydroxy-2-phenyl-7-(6-piperidin-1-yl-hexyloxy)-chromen-4-one (CPP-1)

Step 1:
To a mixture of chrysin I (1 g, 3.93 mole) and anhydrous potassium carbonate (0.81 g, 5.8 mmol) in 20 mL acetone, 1,6-dibromohexane was added. The mixture was refluxed under nitrogen atmosphere for 4 h. After completion of the reaction, potassium carbonate was filtered and washed with excess of acetone (2×50 mL). The combined acetone layers were concentrated under vacuum. The residue was purified by column chromatography on silica gel (60-120 mesh) to yield 7-(6-bromohexyl) chrysin.

Step 2:
To a mixture of 7-(6-bromohexyl) chrysin and anhydrous potassium carbonate (2.41 g, 17.2 mmole) in 20 mL acetonitrile, piperidine was added. The mixture was refluxed under nitrogen atmosphere for 3 h. After completion of the reaction, the reaction mixture was brought to room temperature (25° C.) and was poured into ice water and washed with methylene chloride (2×10 mL). The combined organic layers were dried over anhydrous sodium sulphate and concentrated under vacuum. The residue was purified by column chromatography on silica gel (60-120 mesh) to give 5-hydroxy-2-phenyl-7-(6-piperidin-1-yl-hexyloxy)-chromen-4-one (CPP-1).

Using the method of Example 1, and appropriate reagents, compounds CHM-1, NMC-1 and CHN-1 were similarly prepared.

In another embodiment of the present invention of synthetic analogues, 7-O-hexyl (morpholino) chrysin (Entry No. 1, CHM-1)) have the following spectrochemical and physical properties: Pale yellow solid, mp 103° C., $^1$H NMR (400 MHz, CDCl$_3$): δ 12.74 (1H, s, OH-5), 7.92-7.82 (2H, m, H-2',6'), 7.58-7.44 (3H, m, H-3',4',5'), 6.70 (1H, s, H-3), 6.58 (1H, d, J=1.8 Hz, H-6), 6.40 (1H, d, J=1.8 Hz, H-6), 4.20 (2H, t, J=6 Hz, H-1"), 3.78 (4H, t, H-3''',5'''), 2.40 (4H, t, J=4 Hz, H-2''',6'''), 2.38-2.30 (2H, m, H-6"), 2.0-1.80 (4H, m, H-2"), 1.60-1.55 (2H, m, H-3"), 1.42-1.38 (4H, m, H-4",5"). FABMS: 434 (M$^+$ $^+$1).

In another embodiment of the present invention of synthetic analogues, 7-O-hexyl (N-methyl piperazinyl) chrysin (Entry No. 2, NMC-1) have the following spectrochemical and physical properties: yellow solid, mp 107° C., $^2$H NMR (400 MHz, CDCl$_3$): δ 12.60 (1H, s, OH-5), 7.94-7.82 (2H, m, H-2',6'), 7.58-7.44 (3H, m, H-3',4',5'), 6.62 (1H, s, H-3), 6.42 (1H, d, J=1.8 Hz, H-6), 6.26 (1H, d, J=1.8 Hz, H-8), 4.18 (2H, t, J=6 Hz, H-1"), 2.58-2.30 (8H, m, H-3''',5''' and H-2''',6'''), 2.40 (2H, t, J=4 Hz, H-6"), 2.22 (3H, Me), 1.82-1.78 (2H, m, H-2"), 1.56-1.42 (4H, m, H-4", H-5"), 1.42-1.38 (2H, m, H-3"). FABMS: 447 (M$^+$ $^+$1).

In another embodiment of the present invention of synthetic analogues, 7-O-hexyl (piperidinyl) chrysin (Entry No. 3, CPP-1) have the following spectrochemical and physical properties: Pale yellow solid, mp 108.8° C., $^1$H NMR (300 MHz, CDCl$_3$): δ 12.71 (1H, s, OH-5), 7.90-7.86 (2H, m, H-2',6'), 7.58-7.51 (3H, m, H-3',4',5'), 6.67 (1H, s, H-3), 6.50 (1H, d, J=1.5 Hz, H-6), 6.36 (1H, d, J=1.5 Hz, H-8), 4.0 (2H, t, J=6 Hz, H-1"), 2.80-2.60 (6H, m, H-2''',6''' and H-6"), 1.80-1.60 (4H, m, H-2", H-5"), 1.60-1.20 (10H, m, H-3''', 5''',4'''). FABMS: 422 (M$^+$ $^+$1).

In another embodiment of the present invention of synthetic analogues, 7-O-hexyl (N,N'-dimethylamino) chrysin (Entry No. 4, CHN-1) have the following spectrochemical and physical properties: pale yellow solid, mp 85° C., $^1$H NMR (400 MHz, CDCl$_3$): 8 12.70 (1H, s, OH-5), 7.84-7.88 (2H, m, H-2',6'), 7.52-7.58 (3H, m, H-3',4',5'), 6.70 (1H, s, H-8), 6.48 (1H, s, H-3), 6.38 (1H, s, H-6), 4.12 (2H, t, H-1"), 2.22-2.38 (4H, m, H-2",6"), 2.0 (6H, s, 2×Me), 1.78-1.82 (2H, m, H-5"), 1.44-1.58 (2H, m, H-3"), 1.38-1.42 (2H, m, H-4"). FABMS: 382 (M$^{+++}$1).

Pharmaceutically acceptable salts of the compounds are also within the scope of this invention. The term 'pharmaceutically acceptable salts' refer to an inorganic or organic salt of a compound of the present invention that has properties acceptable for therapeutic use.

Biological Activity

The present invention relates to conferring anti $H.$ $pylori$ activity in some designed semisynthetic flavonoids like 7-O-alkylamino chrysin derivatives (formula $X_1$) and 7-O-acyl oroxylin A derivatives (formula $X_2$). Accordingly, in an embodiment of the present invention, the anti $H.$ $pylori$ activity of 16 such molecules, 2 naturally isolated and 14 semisynthetically designed, were screened by disc diffusion sensitivity assay employing ATCC® standard strains as well as clinical isolates. Based on the observed inhibition zone diameter (see Table 2) as obtained with two doses of the molecules and with majority of the strains, the compounds were grouped into four classes, viz., compounds CPP-1 and CPP-3 as strongly active (3$^+$, diameter>30 mm), compounds CHN-2, CHM-3 and CHN-3 as intermediate active (2$^+$, ~20-30 mm diameter), compounds CHM-1, NMC-1, NMC-2, CPP-2 and NMC-3 as moderately active (1$^+$, ~10-20 mm diameter), and the two natural compounds chrysin and oroxylin A as well as CHN-1, CHM-2, ORC-16 and ORPM-1 as not active (<10 mm diameter). Thus, lack of activity in natural molecules was surmounted by inventing appropriate substitutions like piperidinyl group in $R_2$ position of chrysin core structure as in Formula $X_1$.

In another embodiment of the present invention, the MIC values of all the 10 compounds that have shown some activity in disc diffusion susceptibility test (zone of inhibition>10 mm) were determined by agar dilution method following CLSI® antimicrobial susceptibility testing protocol and employing a panel of clinical isolates and ATCC® standard strains (Table 3a). Compounds like NMC-1, CPP-1, NMC-2, CPP-2 and CPP-3 showed high bacteriostatic activity, CPP-1 being the most potent. An assessment of the MIC range vis-à-vis $MIC_{50}$ values of some potent compounds gave a rank order as: CPP-1 (MIC range 3.125-25 µg/mL, $MIC_{50}$~3.125 µg/mL)>NMC-1 (MIC range 6.25-12.5, µg/mL $MIC_{50}$~6.25 µg/mL)>NMC-2=CPP-2=CPP-3 (MIC range 6.25-100, µg/mL $MIC_{50}$~12.5 µg/mL). Among the other molecules, such values of CHM-1, CHN-2, NMC-3 and CHN-3 were about 6.25-25 µg/mL and 25 µg/mL respectively, and that of CHM-3 was 50-100 µg/mL and 50 µg/mL respectively (Table 3b). The natural molecules chrysin and oroxylin A however showed much higher MIC range and MIC50 values. CPP-1, NMC-1, NMC-2 and CPP-3 exerted potential anti H. pylori activity even in metronidazole-resistant clinical strains, at similar doses, as with other sensitive strains. Such compounds are therefore expected to be effective against drug-resistant as well as sensitive strains of H. pylori thereby achieving one of the objectives of this invention.

In another embodiment of the present invention, the MIC and the MBC values of the four most active compounds, namely, NMC-1, CPP-1, NMC-2 and CPP-3, were further examined by microbroth dilution assay employing one each of clinical strain and ATCC® standard strain (Table 4). Based on both bacteriostatic as well as bactericidal activity, as judged by the two methods and using several H. pylori strains, such four compounds were rank ordered in terms of efficacy as CPP-1>NMC-1>CPP-3>NMC-2.

In yet another embodiment of the present invention, the role of flavone moiety or the n-alkylated amine ring system in manifesting the activity was ascertained. The inhibition zone diameter and the MIC values were determined for five selected molecules containing either the flavone component with ether linked spacer or the n-alkylated amine components attached with spacer (Table 5). All five compounds showed negligible activity confirming the necessity of both the chrysin core structure as well the spacer containing ring systems in manifesting the anti H. pylori activity.

Figures 1, 3A:
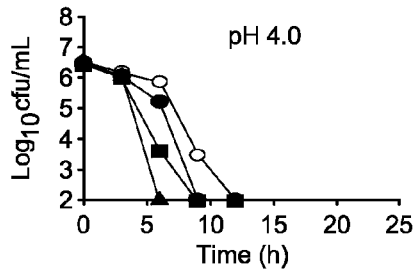
Figures 2, 3A:
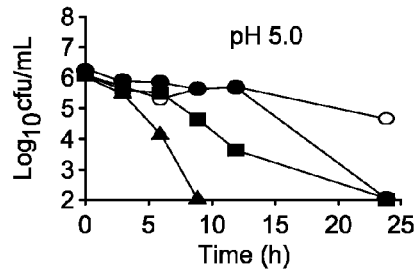
Figures 3, 3A:
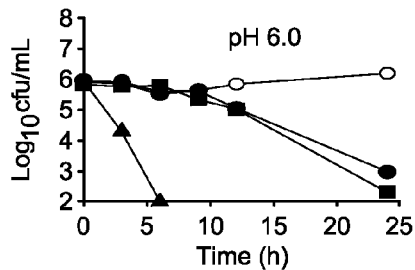

In another embodiment of the present invention, the bactericidal activity of the four potent molecules, CPP-1, NMC-1, NMC-2 and CPP-3, were investigated using time kill assay employing one each of clinical and standard strains of H. pylori (FIG. 1). The series of evidence that have been generated in time- and dose-dependent killing of both clinical as well as standard strains by such molecules, examined around their MIC/MBC values, suggests comparative better efficacy of CPP-1 among all the four compounds.

In yet another embodiment of the present invention, it is demonstrated that a clinical strain HP001 and a standard strain ATCC® 43504, both resistant to metronidazole (MIC for metronidazole are 12.5 and 50 µg/mL respectively), remained susceptible to CPP-1 treatment in vitro. Following repeated, exposure for 10 growth cycles in the presence of sub-MIC dose of CPP-1, there was no significant increase in MIC values, meaning chances of resistance development with CPP-1 treatment is minimal (FIG. 2). Other 3 compounds, namely NMC-1, NMC-2 and CPP-3, did develop some resistance as evident from 4-8 fold increase of their MIC values.

In another embodiment of the present invention, the anti H. pylori potential of CPP-1, NMC-1, NMC-2 and CPP-3 was examined at acidic pH with a view to ascertain their efficacy in stomach acidic environment. Accordingly, the acid stability of the four compounds were examined by exposing them at acidic pH of 2.0 for 2 hours, and then diluting in 96-well microtitre plate to see the changes in MIC and MBC values, if any (Table 6). The activity of CPP-1 remained almost unchanged upon prolonged exposure to acid as evident from just about 2-fold increase in MIC and MBC values, while the other compounds showed relatively higher increase of their MIC/MBC values. This provided clue as to the putative efficacy of CPP-1 in the gastric acidic environment. It was therefore of further interest to examine the killing potential of the most active compound CPP-1 at variable stomach pH ranging 4.0 to 7.2.

In still another embodiment of the present invention, H. pylori standard strain ATCC® 43504 was grown in pH range of 4.0-7.2 by two methods, biphasic culture to investigate long-term killing kinetics and short-time killing kinetics in shake culture media where the liquid media was shaken at 150 rpm to facilitate quick growth of the bacteria. The evidence suggests that the compound CPP-1 is quite effective in killing H. pylori at lower pH values. In biphasic culture media where MBC concentration ranges can be used to demonstrate killing phenomenon, the initial rate of killing at all the concentrations was found to be progressively increasing as the pH goes down indicating strongly that the compound CPP-1 is equally active, if not more, at acidic pH of the stomach (FIG. 3a). This was also evident in short-time kill kinetics study in shake culture media, where higher concentrations of the compound though are necessary (4-8 times MBC dose), albeit during the later phase of the killing (FIG. 3b).

Figures 3, 3A, 4:
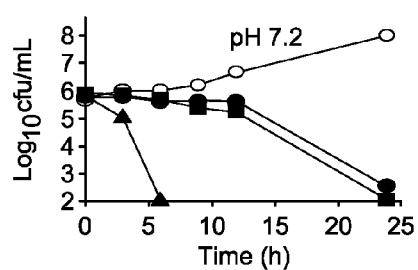
Figures 1, 3B:
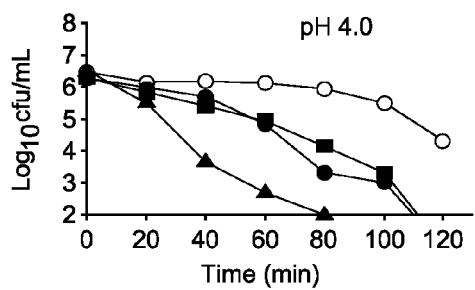
Figures 2, 3B:
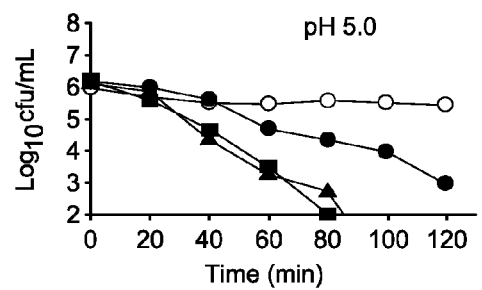
Figures 3, 3B:
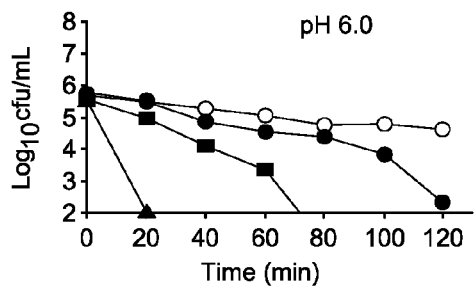
Figures 3, 3B, 4:
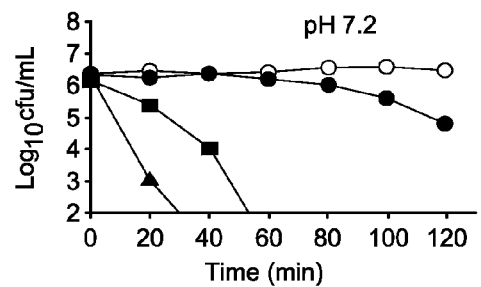

In yet another embodiment of the present invention, the morphological transformation of H. pylori cells from live, rod and spiral shape to non-alive coccoid shape upon exposure to CPP-1 during growth was examined by acridine orange fluorescence staining method (FIG. 4). Progressive transformation of a majority of live and spiral-shaped bacteria (clinical strain HP001) showing orange fluorescence to coccoid-shaped cells exhibiting green fluorescence characteristic of non-alive cells in the presence of increasing concentration of CPP-1 became evident.

In still another embodiment of the present invention, such morphological alterations of H. pylori cells exposed to CPP-1 were examined in transmission electron microscope. Most of the untreated control cells (ATCC® 43504) appeared as slightly curved or straight bacilli. Cultures exposed to two concentrations of CPP-1 for 24 h under microaerophilic conditions at 37° C. revealed only few bacteria with intact shape and structure at 6.25 µg/mL, and at higher dose (12.5 µg/mL), most cells were found to be progressively swollen and destroyed (FIG. 5). The replacement of the normal bacilliform morphology by cell wall blebbing, lytic cells and vesiculation became distinctly apparent.

Further, in an embodiment of the present invention, the effect of the compound CPP-1 was examined for its capacity to inhibit gastric proton pump. Gastric $H^+$ pump ($H^+,K^+$-ATPase) is one of the important targets in designing antisecretory drugs. Using $H^+,K^+$-ATPase rich tubulovesicular and apical membranes, isolated from freshly slaughtered pig gastric mucosa, the effects of different concentrations of CPP-1 on such membrane $H^+,K^+$-ATPase activity was examined in vitro. The observation suggests that the compound CPP-1 at the dose range of 1-10 μg/assay can inhibit $H^+,K^+$-ATPase to an extent of 10-50% (Table 7). Under identical experimental condition omeprazole, the standard medicine used for inhibiting gastric $H^+,K^+$-ATPase activity, inhibits 20-80% of enzyme activity in the same dose range of 1-10 μg/assay. This evidence was taken to mean that the compound has the potential to effectively block gastric $H^+,K^+$-ATPase, and thereby can act as anti-secretory agent.

In yet another embodiment of the present invention, the compound CPP-1 was examined for its capacity to reduce gastric acid secretion. Such experiments can be performed using gastric acid secreting cells, called parietal cell. Live, pure and stimulation-competent gastric parietal cells have been prepared from rabbit gastric mucosa to examine the effect of different concentrations of CPP-1 on acid secreting processes, both basal acid secretion and stimulated acid secretion. Histamine (0.1 mM) was used as physiological secretagogue to stimulate freshly prepared parietal cells in experimental set up. Concentration-dependent strong inhibition of both basal (FIG. 6a) as well as histamine stimulated acid secretion (FIG. 6b), as measured by [$^{14}C$]-aminopyrine uptake ratio, was observed, indicating strong potential of CPP-1 as gastric anti secretory agent. Parallel experiments carried out with two classes of gastric anti secretory medicines, namely, $H_2$ receptor blocker cimetidine, and proton pump inhibitor omeprazole indicated that CPP-1 is better than receptor blocker cimetidine but somewhat less potent than $H^+$ pump inhibitor omeprazole. Thus, gastric anti-secretory property of CPP-1 is evidently proved both in cell-based and enzyme based experimental demonstration, thereby providing strong evidence in support of its use for the treatment of gastric hyperacidity related disorders, including peptic ulcer diseases, gastro esophageal reflux disorders and chronic gastritis.

Further, in an embodiment of the present invention, the compound CPP-1 has been demonstrated to be non-toxic. In acute toxicity study using Swiss albino mice, it is demonstrated that CPP-1 up to a dose of 0.5 g/kg of body weight, did not show any mortality, and the animals remained completely healthy after 15 days.

EXAMPLE 2

Description of Biological Experiments

Experiment 1

Anti *H. pylori* Screening by Disc Diffusion Susceptibility Assay

The anti *H. pylori* activity of all 16 flavonoid molecules, 2 naturally isolated and 14 synthetic derivatives, was screened by disc diffusion sensitivity assay employing 2 clinical strains HP001 and HP002, and three standard strains ATCC® 700392, 43504 and 49503. A 0.5 mL inoculum ($10^8$ CFU/mL) for each bacterial strain tested was flooded on freshly prepared Brain Heart Infusion (BHI) agar plates supplemented with 7% FCS, 0.5% IsoVitalex and 0.0025% DENT® and the discs (5 mm diameter) containing different compounds or antibiotics (dissolved either in ethanol or DMSO) were placed on the agar surface. After incubation for 3 days in a microaerophilic atmosphere at 37° C., the diameter of the zone of inhibition was measured (Glupczynsky, 1996; McNulty et al., 2002). Clarithromycin showed inhibition zone of 18 mm for the strains HP001 and HP002 at 0.01 mg/disc and that of 28, 20 and 15 mm respectively with strains 700392 (0.4 mg/disc), 43504 (0.04 mg/disc) and 49503 (0.005 mg/disc). Amoxycillin gave inhibition zone diameter of 10-16 mm with clinical strains at 0.16 mg/disc and about 13-15 mm with standard strains at 0.5-1.0 mg/disc.

Based on the observed inhibition zone diameter as obtained with two doses of the molecules (100 and 200 μg/disc) and with majority of the strains (Table 2), the compounds were grouped into four classes: (i) compounds CPP-1 and CPP-3 as strongly active (diameter>30 mm) and were given a score of $3^+$, (ii) compounds CHN-2, CHM-3 and CHN-3 as intermediate active (~20-30 mm diameter) and were given a score of $2^+$, (iii) compounds CHM-1, NMC-1, NMC-2, CPP-2 and NMC-3 as moderately active (~10-20 min diameter) and were given a score of $1^+$, and (iv) the two natural compounds chrysin, and oroxylin A as well as CHN-1, CHM-2, ORC-16 and ORPM-1 as not active (>10 mm diameter). There was not much strain specific variation with all the molecules, excepting with compounds CPP-1, CHN-2, CPP-3 and CHN-3 wherein we found a maximum of about 10 mm difference in zone diameters (Table 2).

TABLE 2

Anti *H. pylori* activity of the compound analogues

| Entry | | Inhibition zone diameter (score) | | | | |
|---|---|---|---|---|---|---|
| | | Clinical strain | | ATCC standard strain | | |
| No. | Sample | HP001 | HP002 | 700392 | 43504 | 49503 |
| I | Chrysin | Nil | Nil | Nil | Nil | Nil |
| 1 | CHM-1 | + | + | + | Nil | + |
| 2 | NMC-1 | + | ++ | + | + | + |
| 3 | CPP-1 | ++ | +++ | ++ | ++ | +++ |
| 4 | CHN-1 | Nil | Nil | Nil | Nil | Nil |
| 5 | CHM-2 | Nil | Nil | Nil | Nil | Nil |
| 6 | NMC-2 | + | ++ | + | + | + |
| 7 | CPP-2 | + | + | + | + | + |
| 8 | CHN-2 | ++ | ++ | + | ++ | ++ |
| 9 | CHM-3 | ++ | ++ | + | + | ++ |
| 10 | NMC-3 | + | ++ | + | + | + |
| 11 | CPP-3 | ++ | +++ | ++ | ++ | ++ |
| 12 | CHN-3 | ++ | ++ | + | + | ++ |
| II | Oroxylin A | Nil | Nil | Nil | Nil | Nil |
| 13 | ORC-16 | Nil | Nil | Nil | Nil | Nil |
| 14 | ORPM-1 | + | Nil | Nil | Nil | Nil |

Experiment 2

Anti *H. pylori* Spectrum by Agar Dilution Method

MICs were determined against a panel of 6 clinical isolates (HP001, HP002, HP003, HP004, HP005 and HP006), and 4 standard strains in BHI agar plates following essentially CLSI® antimicrobial susceptibility testing method (Glupczyriski et al., 2002; Best et al., 2003). Essentially, the strains employed for the evaluation were clarithromycin and amoxicillin sensitive. The standard strain ATCC® 43504 and all six clinical strains were metronidazole resistant, but standard strains ATCC® 700392, 49503, and 43629 were metronidazole sensitive. Plates contained two-fold serial dilutions of the compounds ranging from 1.56-100 ng/mL. Five microlitres of 3-day old freshly grown *H. pylori* culture (~$10^8$ CFU/mL) was inoculated onto drug-containing BHI agar plates supplemented with 7% FCS, 0.5% IsoVitalex and 0.0025% DENT®, which were then incubated for 3 days under microaerophilic condition at 37° C. The MIC was defined as the lowest concentrations that completely inhibited the development of visible growth on the agar plates, and were determined in duplicate for each strain.

The MIC values of all the 10 molecules that have shown some activity were evaluated by agar dilution method (Table 3a). The results indicated potential bacteriostatic activity in compounds like NMC-1, CPP-1, NMC-2, CPP-2 and CPP-3. Somewhat good activity of the molecules NMC-3 and CHN-3 was also noted. Such MIC data correlated well with the values obtained by disk diffusion sensitivity assay. An assessment of the $MIC_{50}$ values (Table 3b) of some potent compounds gave a rank order: CPP-1 (~3.125 µg/mL) >NMC-1 (~6.25 µg/mL)>NMC-2=CPP-3=CPP-2 (~12.5 µg/mL). Among the other molecules, such $MIC_{50}$ value of the compounds CHM-1, CHN-2, CHN-3 and NMC-3 was about 25 µg/mL, and that of compound CHM-3 were approximately 50-100 µg/mL. The molecules chrysin, oroxylin A and its two semisynthetic derivatives, showed much higher $MIC_{50}$ values. We have also determined MIC values of the standard antibiotics, clarithromycin, amoxycillin and metronidazole against the clinical isolates and the standard strains (Table 3a).

Experiment 3

Determination of MIC and MBC Values by Microbroth Dilution Assay

Based on disc diffusion sensitivity and MIC values both, the four most active compounds, namely, NMC-1, CPP-1, NMC-2 and CPP-3 were considered for further evaluation. In microbroth dilution assay employing one clinical and one standard strain, both the bacteriostatic and the bactericidal values were determined for all four compounds as well as for clarithromycin (Table 4). Two-fold serial dilutions were prepared in 96-well microtitre plate containing a total volume of 0.1 mL Mueller Hinton broth supplemented with 5% FCS. A 3-day old liquid culture was diluted 10 times in Mueller Hinton broth and 0.1 mL of these cultures was inoculated into each well to give a final concentration of ~$10^6$ CFU/mL. The plates were incubated for 3 days in a microaerophilic atmosphere at 37° C. Following incubation, the plates were examined visually, and the lowest concentration showing complete inhibition of growth was recorded as the MIC of the respective compound (Hachem et al., 1996). Aliquots (0.1 mL) of 72-h culture in which no growth had been detected were taken from the wells of the above TABLE 3a Anti. *H. pylori* spectrum by agar dilution method

| | MIC (µg/mL) | | | | | | | | | |
|---|---|---|---|---|---|---|---|---|---|---|
| | Clinical strain | | | | | | Standard strain | | | |
| Compound | HP001 | HP002 | HP003 | HP004 | HP005 | HP006 | 43504 | 49503 | 700392 | 43629 |
| CHM-1 | 25 | 25 | <12.5 | <12.5 | <12.5 | <12.5 | 25 | 25 | 25 | 25 |
| NMC-1 | 12.5 | 6.25 | <6.25 | <6.25 | <6.25 | <6.25 | <12.5 | 6.25 | 12.5 | 12.5 |
| CPP-1 | 6.25 | 6.25 | <3.125 | <3.125 | <3.125 | <3.125 | 6.25 | 6.25 | 3.125 | 25 |
| NMC-2 | 12.5 | 6.25 | 12.5 | 12.5 | 6.25 | 12.5 | 12.5 | 3.125 | 12.5 | 25 |
| CPP-2 | 25 | 25 | <12.5 | <12.5 | <12.5 | <12.5 | 12.5 | 25 | 25 | 100 |
| CHN-2 | 25 | 25 | 12.5 | 12.5 | 25 | 25 | 50 | 25 | 50 | 12.5 |
| CHM-3 | 50 | 50 | 100 | 100 | 100 | 100 | 50 | 50 | 50 | 100 |
| NMC-3 | 25 | 25 | <12.5 | <12.5 | <12.5 | <12.5 | 25 | 25 | 25 | 25 |
| CPP-3 | 25 | 25 | <12.5 | <12.5 | <12.5 | <12.5 | 12.5 | 25 | 25 | 100 |
| CHN-3 | 25 | 25 | <12.5 | <12.5 | <12.5 | <12.5 | 25 | 25 | 25 | 25 |
| Clarithromycin | 0.016 | 0.032 | <0.02 | 0.04 | 0.08 | 0.08 | 0.032 | 0.016 | 0.064 | 0.1 |
| Amoxicillin | 0.032 | 0.032 | 0.016 | 0.016 | 0.016 | 0.016 | 0.0625 | 0.032 | 0.0625 | 0.032 |
| Metronidazole | 12.5 | >100 | 100 | 100 | 25 | 25 | 50 | 1.56 | 1.56 | 1.56 |

TABLE 3b

MIC range and $MIC_{50}$ of active compounds

| | MIC (µg/ml) | |
|---|---|---|
| Compound | Range | $MIC_{50}$ |
| CHM-1 | 6.25-25 | 25 |
| NMC-1 | 6.25-12.5 | 6.25 |
| CPP-1 | 3.125-25 | 3.125 |
| NMC-2 | 3.125-12.5 | 12.5 |
| CPP-2 | 6.25-100 | 12.5 |
| CHN-2 | 12.5-50 | 25 |
| CHM-3 | 50-100 | 50 |
| NMC-3 | 6.25-25 | 25 |
| CPP-3 | 6.25-100 | 12.5 |
| CHN-3 | 6.25-25 | 25 |
| Clarithromycin | 0.016-0.1 | 0.032 |
| Amoxicillin | 0.016-0.0625 | 0.032 |
| Metronidazole | 1.56->100 | 50 | microtitre plates and used to streak on fresh BHI agar plates. MBCs were determined by visual inspection of such plates after further incubation for 72 h at 37° C. and the titre-point where no growth (less than 10 colonies) appeared was considered as the MBC.

The compound CPP-1 showed lowest MIC and MBC values of ~6.25 µg/mL with standard strain 43504 (Table 4). None of the other three molecules showed such low MIC and MBC values considering the data obtained with both the strains. However, with clinical strain HP001, both the compounds CPP-1 and NMC-1 appear to have shown similar potency (MIC 6.25 µg/mL and MBC 12.5 µg/mL) and the compounds NMC-2 and CPP-3 exhibited a 2-fold lower potency. The compound CPP-1 was found to kill the standard strain ATCC® 43504 below 6.25 µg/mL. But for killing the clinical strain a 2-fold dose i.e., 12.5 µg/mL was required. Employing the same dose, bacteriostatic but not the bactericidal activity could be achieved with other compounds like NMC-1, NMC-2 and CPP-3 (Table 4).

TABLE 4

Determination of MIC and MBC by microbroth dilution method

| Sample | MIC (µg/mL) | | MBC (µg/mL) | |
| --- | --- | --- | --- | --- |
| | HP001 | ATCC 43504 | HP001 | ATCC 43504 |
| NMC-1 | 6.25 | 6.25 | 12.5 | 25 |
| CPP-1 | 6.25 | 6.25 | 12.5 | <6.25 |
| NMC-2 | 12.5 | 12.5 | 25 | 50 |
| CPP-3 | 12.5 | 12.5 | 25 | 25 |
| Clarithromycin | 0.01 | 0.04 | 0.04 | 0.08 |

Experiment 4

Anti *H. pylori* Activity of the Spacer Group

It was of necessity to determine the role of the substituted cyclohexane ring system attached to chrysin core structure through 3 C, 4 C and 6 C spacers in manifesting the anti *H. pylori* activity. Thus the activity of five such molecules was investigated against *H. pylori* employing disc diffusion sensitivity assay and MIC determination by microbroth dilution assay. As evident from Table 5, none of the spacers bearing morpholinyl, N-methyl piperazinyl or piperidinyl showed any anti *H. pylori* activity. Also, the withdrawal of the OH group from the 5-position of the parent chrysin ring system resulted loss in anti *H. pylori* activity.

Experiment 5

Time Kill Kinetic Analyses of the Four Active Compounds CPP-1, NMC-1, CPP-3 and NMC-2

The bactericidal activity of the four potent molecules was further investigated using time kill assay employing one clinical and a standard strain (FIG. 1). The rate of bacterial killing by four compounds at 0.5'-, 1'-, 2'- and 4'MIC dose against log phase cultures containing ~$10^6$ cells/mL were determined over 36 h in biphasic culture media (Wang & Huang, 2005). Briefly, *H. pylori* was grown in a 50-mL flask containing biphasic medium consisting of 5 mL BHI agar supplemented with 7% FCS, 0.5% Isovitalex and 0.0025% DENT® plus 5 mL *Brucella* broth containing 5% FCS. Five mL of molten BHI agar was poured at the bottom of the flask and the compounds were added at appropriate concentration. On cooling, when a solid plate was formed at the bottom of the flask, 4 mL *Brucella* broth was poured over the agar and same amount of sample as added into agar was added in the broth. The experiment was initiated by adding 1 mL (~$10^6$ CFU/mL) of 24-h culture, grown under similar biphasic condition, to the experimental flasks, kept in microaerophilic condition at 37° C. At 0, 3, 6, 9, 12 and 24 h, 0.1 mL of culture was taken out, appropriately diluted and streaked onto fresh BHI agar plate to determine viable counts. The rates of killing were determined by measuring the decrease in viable bacteria ($\log_{10}$ CFU/mL) in presence of increasing concentrations of the compounds. The minimum detection level was 100 CFU/mL. Viable count determinations of

TABLE 5

Anti *H. pylori* activity evaluation of the spacer molecules by disc diffusion sensitivity assay and microbroth dilution assay

| Spacer | Inhibition Zone Diameter (mm) | | MIC (µg/mL) | |
| --- | --- | --- | --- | --- |
| | HP001 | ATCC 43504 | HP001 | ATCC 43504 |
| 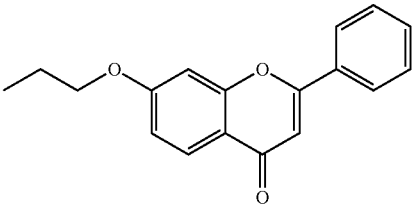 [SMILES: CCCOc1ccc2c(=O)cc(-c3ccccc3)oc2c1] | Nil | Nil | >400 | >400 |
| 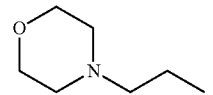 | Nil | Nil | >400 | >400 |
| 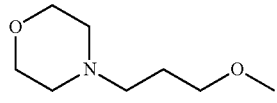 | Nil | Nil | >400 | >400 |
| 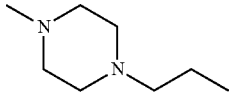 | Nil | Nil | >400 | >400 |
| 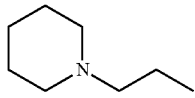 | Nil | Nil | >400 | >400 |

'Nil' means zone of inhibition below 10 mm.

control cultures with either DMSO or ethanol were indistinguishable from the 'solvent-free-control' values. The effect of clarithromycin was also studied under similar experimental condition.

With clinical strain HP001, clarithromycin could not produce any inhibition of cell growth within 6 h (FIG. 1, panel e) even at 4'MIC dose. At around 9 h, the inhibition was somewhat prominent, causing 1-log decrease in cell count. However, at all 3 concentrations, the viable cell count drastically lowered down to $10^2$ CFU/mL within 24 h. The killing kinetics of the four most active compounds NMC-1, CPP-1, NMC-2 and CPP-3 were studied under similar experimental conditions as with standard antibiotics. With compound CPP-1, dose-dependent killing was observed within 6 h (panel a). The lower dose (1×MIC), although caused bacterial killing to some extent, was not high enough to produce total bactericidal activity. With compound NMC-1 at 12.5 µg/mL, complete bactericidal effect (a 4-log decrease in cell count) within 12 h was noted (panel b). The MIC dose (6.25 µg/mL) could not however exert complete killing even at 36 h. With compound NMC-2 (panel c), the killing effect was evident only after 9 h of incubation. The MIC dose (12.5 µg/mL) once again did not kill the bacteria completely even at 36 h, whereas the next higher dose (25 µg/mL) could produce bactericidal activity (a 4-log decrease) within 24 h. Compound CPP-3 at MIC dose could not exert any effect on bactericidal activity. The 2×MIC dose (25 µg/mL) was however sufficient to kill the bacteria (4-log decrease) within 12 h (panel d).

Using standard strain ATCC® 43504, the time kill assay with same 4 compounds CPP-1, NMC-1, NMC-2 and CPP-3 along with clarithromycin was carried out. Clarithromycin at 0.08 µg/mL did exert complete killing (4-log decrease in cell count) within 24 h. Compound CPP-1, at 0.5×MIC (3.125 µg/mL), could produce only f-log decrease in cell count within 36 h while at 1×MIC (6.25 µg/mL) and at MBC value (i.e., 2×MIC), it exhibited complete killing within 36 h and 24 h respectively (panel f). Compound NMC-1 produced only 1-log decrease in cell count within 36 h at MIC value (6.25 µg/mL) while at 2×MIC (i.e., MBC; 12.5 µg/mL), complete killing of bacteria was observed within 24 hour (panel g). The MIC dose of compound NMC-2 (12.5 µg/mL) could not produce complete killing of the standard strain, but at MBC (25 µg/mL) a complete killing effect was observed well within 12 h (panel h). Compound CPP-3 has no killing potency at MIC (12.5 µg/mL). The next two higher doses (25 µg/mL and 50 µg/mL) could however kill the bacteria totally in about 12 h, the rate of killing being slightly different between the low and high dose (panel i).

Experiment 6

Induction of Drug Resistance by CPP-1, NMC-1, NMC-2 and CPP-3

To investigate the development of drug resistance, CPP-1, NMC-1, NMC-2 and CPP-3 were prepared as 2-fold serial dilutions with medium in 96-well microtitre plates. *H. pylori* strains, one clinical HP001 and one standard ATCC® 43504, were inoculated into each dilution series at an inoculum size of ~$10^6$ CFU/well. After 3 days of incubation, the culture from each series with the highest concentrations of the compound and also showing turbidity was subcultured in a fresh series of the same drug. This procedure was repeated for up to 10 cycles, and alterations in MIC values during the course of continued exposure were determined (Iwao et al., 2004).

The repeated transfer (10 times) of the standard as well as the clinical strain (both metronidazole resistant) in the drug containing media produced no significant increase in MIC values for CPP-1 (only 2-fold increase in MIC value), while somewhat higher increase of the MIC values was observed with other 3 compounds (FIG. 2). This is taken to mean that CPP-1, as compared with other three molecules, is better as far the chance of resistance development is concerned.

Experiment 7

Acid Stability Study of CPP-1, NMC-1, NMC-2 and CPP-3

A 100 µL stock of CPP-1, NMC-1, NMC-2 and CPP-3 (1-2 mg/mL) was treated with 20-30 µL of 0.12 NHCl to bring the pH of the solution to ~2.0, and kept at 25° C. for 2 h (Funatogawa et al., 2004). Such acid-treated samples were then serially diluted (2 fold) with medium in 96-well microtitre plates to determine the MIC and the MBC values by microbroth dilution assay as detailed under Experiment 3.

The activity of CPP-1 remained almost unchanged upon prolonged exposure to acid as evident from just about 2-fold increase in MIC and MBC values, while the other compounds showed relatively higher increase of their MIC/MBC values (Table 6).

TABLE 6

Acid stability study of CPP-1, NMC-1, NMC-2 and CPP-3

| | MIC (mg/mL) | | | | MBC (mg/mL) | | | |
| --- | --- | --- | --- | --- | --- | --- | --- | --- |
| | Control | | Acid treated | | Control | | Acid treated | |
| Sample | HP001 | 43504 | HP001 | 43504 | HP001 | 43504 | HP001 | 43504 |
| CPP-1 | 6.25 | 6.25 | 12.5 | 12.5 | 12.5 | <6.25 | <12.5 | 25 |
| NMC-1 | 6.25 | 6.25 | 12.5 | 25 | 12.5 | 25 | 25 | <25 |
| NMC-2 | 12.5 | 12.5 | 25 | 25 | 25 | 50 | 50 | <50 |
| CPP-3 | 12.5 | 12.5 | 25 | 50 | 25 | 25 | 50 | <50 |

Experiment 8a

Effect of CPP-1 on *H. pylori* Kill Kinetics in Biphasic Culture at Different pH The decrease in viable cell count during exposure to CPP-1 was evaluated as a function of time at different low pH values (citrate buffer for pH 4.0 and 5.0 and citrate-phosphate buffer for pH 6.0) using biphasic culture. A 24-h culture broth of *H. pylori* ATCC® 43504 (obtained from biphasic culture) was inoculated into *Brucella* broth containing CPP-1 at different concentrations in biphasic culture. The bacterial suspension was incubated in microaerophilic environment at 37° C., and samples were taken to determine viable counts at 0, 3, 6, 9, 12 and 24 h after drug exposure.

At low pH, CPP-1 was found to provide potentiation of the *H. pylori* killing activity at its MIC/MBC concentration ranges; the efficacy was more in pH 4.0 and 5.0 as compared to pH 6.0 and 7.0. The MBC concentration of 12.5 µg/mL was enough to kill all the bacteria within 10-12 h at pH 4.0 while at higher pH values, the same concentration produced killing only after 24 h (FIG. 3a). Comparing the early phase kill kinetics where there was not much decrease in viable cell count at lower pH values in control system, the phenomenon is quite evident. This provided clue as to the possibility of the effectiveness of the compound CPP-1 at acidic environment of the stomach.

Experiment 8b

Effect of CPP-1 on *H. pylori* Kill Kinetics in Shake Culture at Different pH upon Short Time Exposure The decrease in viable cell count during exposure to high concentrations of CPP-1 in short time kill kinetics assay was also evaluated at different acidic pH values of 4.0, 5.0 and 6.0 (citrate buffer for pH 4.0 and 5.0 and citrate-phosphate buffer for pH 6.0). A 24-h culture broth of *H. pylori* ATCC® 43504 was inoculated into *Brucella* broth containing CPP-1 at different concentration. The bacterial suspension was incubated in microaerophilic environment at 37° C. with shaking at 150 rpm, and samples were taken at 0, 20, 40, 60, 80, 100 and 120 min after drug exposure to determine viable counts.

The effect of CPP-1 at higher concentrations 50, 100 and 150 mg/mL was studied at different pH upon short exposure to ATCC® 43504. At 50 mg/mL, a 3-log decrease of growth was observed in the pH 4.0, 5.0 and 6.0 whereas the bacteria survived at pH 7.2 at such concentration (FIG. 3b). However, at higher doses of 100 and 150 mg/mL, the rate of killing was found to increase as the pH of the media raised.

Experiment 9

Fluorescence Microscopic Evidence on the Morphological Transformation of *H. pylori* Upon Exposure to CPP-1

For the purpose of fluorescence staining, a bacterial smear was prepared, fixed with methanol for 2 min, stained with 0.1% acridine orange solution for 2-3 min, rinsed thoroughly with distilled water (Haqqani, 2001) and observed under fluorescence microscopy using 1-3 filter (emission wavelength 510 nm). The live organism appeared as orange color in the dark background and the non-viable cells as green (Shirai et al., 2000).

The morphological alterations of the clinical strain (HP001) exposed to 3.125, 6.25 and 12.5 mg/mL of CPP-1 for 24 h as observed under fluorescence microscopy are shown in FIG. 4. As evident from panel A, the control cells appeared as spiral and rod shaped, orange in colour and huge in numbers at the end of 24-h culture. The cells upon 24-h exposure to lowest concentration of CPP-1, resembled almost like control with some deformation (Panel B). Exposure of the cells to higher concentrations of 6.25 and 12.5 mg/mL for 24 h resulted in progressively deteriorating cell population leading to more of non-viable cells (green fluorescence) and coccid formation (Panels C and D respectively).

Experiment 10

Electron Microscopic Evidence on the Morphological Transformation of *H. pylori* upon Exposure to CPP-1

The morphological alteration of *H. pylori* cells (ATCC® 43504) exposed to various concentrations of CPP-1 was further examined using transmission electron microscopy (Dai et al., 2005). After exposure to CPP-1 at 0, 6.25 and 12.5 µg/mL for 24 h under microaerophilic conditions at 37° C., cells were harvested by centrifugation, fixed with glutaraldehyde and postfixed with osmium tetroxide. Samples were dehydrated, embedded in SPUR, sections cut and applied to copper grids. The grids were contrasted with uranyl acetate and lead citrate and the sections were examined on a transmission electron microscope.

The morphological alterations of *H. pylori* cells exposed to 6.25 µg/mL (B) and 12.5 µg/mL (C) of CPP-1 as compared with control (A) are evident (FIG. 5). Transmission electron micrographs demonstrated that CPP-1 treatment induced swelling and vacuole like structures in the cytoplasm of *H. pylori* cells. The phenomenon was concentration dependent, and exposure to 6.25 or 12.5 µg/mL of CPP-1 transformed the shape and size of the organism from baciliform to doughnut-shaped form. The rupture of the bacilli to coccoid form was evident to some extent, even at concentration of 6.25 µg/mL (MIC dose). The bacterium lost its structure at higher concentrations (6.25-12.5 µg/mL) and the drug-induced destruction was evident. Moreover, the outer envelop of an atypical shaped organism was detached from the inner side of the bend.

Experiment 11

Effect of CPP-1 on Gastric $H^+,K^+$-ATPase Activity

The effect of CPP-1 on gastric $H^+K^+$-ATPase was investigated. Isolation of pig gastric mucosal membranes, rich in $H^+,K^+$-ATPase activity, was carried out by density gradient centrifugation technique (Ray, 1978). The enzyme assay system contained 10 mM PIPES-Tris (pH 6.8), 2 mM each of ATP and MgCl with or without 10 mM KCl and about 10 mg membrane protein in a final volume of 1 mL. Both blank and experimental tubes with or without CPP-1 at different concentrations were preincubated with otherwise complete assay mixture at 37° C. for 10 min before initiating the reaction with the substrate ATP. After appropriate time of incubation with ATP at 37° C., the reaction was terminated with the addition of 1 mL of ice-cold TCA (14%, w/v). The liberated inorganic phosphate (Pi) was estimated essentially by the method of Sanui (1974). $K^+$-stimulated activity referred to as $H^+,K^+$-ATPase activity, was calculated as the difference between the activity in presence of $Mg^{2+}$ plus $K^+$ and the basal activity ($Mg^{2+}$-ATPase) in presence of $Mg^{2+}$ alone. The specific activity of $H^+,K^+$-ATPase was expressed as micromoles of Pi liberated per hour per milligram protein. The data are averages of 3-4 determinations each carried out in triplicate. The specific activity of $H^+,K^+$-ATPase in control sets was in the range of 40-50 µmole Pi/mg protein/h.

CPP-1 was found to inhibit gastric $H^+,K^+$-ATPase activity in vitro in a dose dependent manner. About 50% inhibition was observed in the concentration range of 10 mg/assay (Table 7). The standard medicine omeprazole, under similar experimental condition produced about 80% inhibition of such $H^+,K^+$-ATPase.

TABLE 7

Effect of CPP-1 on pig gastric $H^+$, $K^+$-ATPase activity

| Compound | Concentration (mg/assay) | Percent inhibition of $H^+$, $K^+$-ATPase activity |
|---|---|---|
| CPP-1 | 1 | 20 |
|  | 5 | 30 |
|  | 10 | 50 |
| Omeprazole | 1 | 20 |
|  | 10 | 80 |

Experiment 12

Effect of CPP-1 on Basal and Histamine-Stimulated Acid Secretion in Gastric Parietal Cell Parietal cells (PC) were isolated from New Zealand White rabbits (weighing ~2.5 kg) essentially according to Berglindh (1984) and as modified by Mazzeo et al. (1988). The PC preparations were nearly 90% pure and viable. The effect of CPP-1 on basal and histamine stimulated acid secretion in parietal cells was examined as follows. The PC suspension was incubated for 10 min at 37° C. with gentle stirring and continuous slow top gassing with oxygen. The [$^{14}$C]-aminopyrine (115 mCi/mmole) was added to the suspension at 0.1 mCi/mL, and incubation was continued for another 10 min. One-milliliter aliquot of PC (~$5 \times 10^6$ cells) was added to various concentrations of CPP-1 in the presence and the absence of histamine (0.1 mM) and incubated for 20 min at 37° C. with slow shaking and oxygen top gassing. At the end of the incubation, the PC suspensions were centrifuged, supernatant carefully aspired off and the pellets solubilized in scintillation fluid containing Triton X-100. The resulting solution was counted in a liquid scintillation counter. The aminopyrine accumulation was determined as the ratio of intra- to extracellular aminopyrine according to Mazzeo et al. (1988).

The effect of varied concentrations of CPP-1 on basal acid secretion in such freshly prepared parietal cells was examined. The basal acid secretion was decreased in a dose dependent manner upon exposure to CPP-1 (FIG. 6a). A 50% reduction in basal acid secretion was obtained at about 5 µg/mL CPP-1. The compound appeared to be much more potent than cimetidine, and about 2-3 fold less potent than omeprazole in inhibiting basal acid secretion in PC, indicating its efficacy in managing basal hyperacid secretion. The compound CPP-1 was further examined for its effect on histamine stimulated (0.1 mM) acid secretion. It exhibited a dose-dependent inhibition of histamine-stimulated acid secretion (FIG. 6b) with an $IC_{50}$ value of about 15 µg/mL. The compound CPP-1 was found to be more active than cimetidine in inhibiting histamine-stimulated secretion but about 5-fold less potent than omeprazole. Thus, the compound CPP-1 was observed to be effective in blocking both basal and histamine stimulated acid secretion.

Experiment 13

Toxicity Evaluation for the Potent Compound CPP-1

The most potent compound CPP-1 was checked for mortality of the Swiss albino mice. Five animals of Swiss albino mice strain were used for this purpose. The dosage up to 0.5 g/kg body weight given orally per mice and the animals were kept for 15 days under observation. It was observed that the mice were not affected at the dose level of 0.5 g/kg body weight of CPP-1. No mortality and behavioral abnormality was noted.

Advantages

The semisynthetic molecule CPP-1 [7-O-(6-piperidin-1-yl-hexyl)-chrysin], confirred with bi-functional activity, can be prepared commercially starting from chrysin and piperidine, abundantly present in various plants (already published).

The compound is not toxic.

Peptic ulcer disease is a multietiologic disease. This designed molecule is capable of acting simultaneously against the bug *H. pylori* and the hypersecretion of gastric HCl, the two major etiologies of peptic ulcer diseases.

Unlike currently available modern medicines which require triple or quadruple therapy involving 1-2 antibiotics like clarithromycin, amoxicillin, metronidazole, one antisecretory drug like $H_2$ receptor blocker or gastric H' pump inhibitor and one mucus coating agent, the molecule CPP-1 is-unique in the sense that it is strong anti *H. pylori* and also gastric antisecretory.

The most active compound CPP-1 appears to possess high therapeutic potential as it is endowed with a 6 C lipophilic spacer in its side chain which would make the compound membrane permeable.

Unlike clarithromycin which is effective only at neutral pH in eradicating *H. pylori*, the molecule CPP-1 is effective both at acidic and neutral pH.

Unlike metronidazole towards which *H. pylori* develops resistance upon long-term use, the chances of resistance development to CPP-1 is minimal.

The most active compound CPP-1 is effective even against metronidazole-resistant strains.

REFERENCES

1. Ali R M, Houghton P J, Raman A and Hoult J R S. (1998). Antimicrobial and anti-inflammatory activities of extracts and constituents of *oroxilum indicum*. Phytomedicine 5:375-81.
2. Arcari G, Bernardi L, Falconi G, Scarponi U. (1980). 4,5,6,7-Tetrahydroimidazo-[4,5-c]-pyridine derivatives. U.S. Pat. No. 4,223,146.
3. Ares J J, Kakodkar S V, Kelm G R, Murray P D, Randall J L, Slough C L. (1995). Use of flavone derivatives for gastroprotection. U.S. Pat. No. 5,399,584.
4. Babu K S, Babu T H, Srinivas P V, Sastry B S, Kishore K H, Murty U S N, Rao J M (2005). Synthesis and in vitro study of novel 7-O-acyl derivatives of Oroxylin A as antibacterial agents. Bioorganic and Medicinal Chemistry Letters 15:3953-56.
5. Babu K S, Babu T H, Srinivas P V, Kishore K H, Murty U S N, Rao J M. (2006). Synthesis and biological evaluation of novel C (7) modified chrysin analogues as anti bacterial agents. Bioorganic and Medicinal Chemistry Letters 16:221-4.
6. Beil W, Birkholz C, Sewing K-Fr. (1995). Effect of flavonoids on parietal cell acid secretion, gastric mucosal prostaglandin production and *Helicobacter pylori* growth. Arzneimittelforschung 45:697-700.

7. Berglindh T. (1984). The mammalian gastric parietal cell in vitro Annual Review Physiology 46:377-92.
8. Best L M, Haldane D J, Keelan M, Taylor D E, Thomson A B, Loo V, Fallone C A, Lyn P, Smaill F M, Hunt R, Gaudreau C, Kennedy J, Alfa M, Pelletier R, Veldhuyzen van zanter S J (2003). Multilaboratory comparison of proficiencies in susceptibility testing of *Helicobacter pylori* and correlation between agar dilution and E-test methods. Antimicrobial-Agents and Chemotherapy 47:31388-44.
9. Borody T J. (1993). Method for treatment of gastro intestinal disorders. U.S. Pat. No. 5,196,205.
10. Buckler R T, Ward F E, Garling D L. (1980). 3-Methylene flavanones and 3-methylene chromanones. U.S. Pat. No. 4,241,069.
11. Bullard W. (1997). Peptic Ulcer Diseases, US National Community Pharmacists Association.
12. Catrenich C E, Nelson D G A. (1995). Methods and compositions of diphenyl ether phosphate esters for the treatment of gastrointestinal disorders. U.S. Pat. No. 5,447,923.
13. Cereda E, Donetti A, Giachetti A, Del Soldato P. (1987). Substituted heterocyclyl-phenyl-(sulfonyl- or phosphonyl)-amidines. U.S. Pat. No. 4,643,993.
14. Cushnie T P, Lamb A J. (2005). Antimicrobial activity of flavonoids. International Journal Antimicrobial Agents 26:343-56.
15. Dai G, Cheng N, Dong L, Muramatsu M, Xiao S, Wang M W, Zhu D X. (2005). Bactericidal and morphological effects of NE-2001, a novel synthetic agent directed against *Helicobacter pylori*. Antimicrobial Agent and Chemotherapy 49:3468-73.
16. Das P K, Goswami S, Chinniah A, Panda N, Banerjee S, Sahu N P, Achari B. (2007a). Woodfordia fruticosa: Traditional Uses and Recent Findings. Journal of Ethnopharmacology (2007) 110:189-199.
17. Das P K, Sahu N P, Banerjee S, Sett S, Goswami S, Bhattacharya S. (2007b). Anti-peptic ulcer activity of an extract of a flower of Woodfordia fruticosa. U.S. Pat. No. 7,291,353.
18. Everhart J E. (2000). Recent developments in the epidemiology of *Helicobacter pylori*. Gastroenterology Clinics of North America 29:559-78.
19. Fukai T, Marumo A, Kaitou K, Kanda T, Terada S, Nomura T. (2002). Anti-*Helicobacter pylori* flavonoids from licorice extract. Life Science 71:1449-63.
20. Funatogawa K, Hayashi S, Shimomura H, Yoshida T, Hatano T, Ito H, Hirai Y. (2004). Antibacterial activity of hydrolyzable tannins derived from medicinal plants against *Helicobacter pylori*. Microbiology and Immunology 48:251-61.
21. Glupczynski Y (1996). Culture of *Helicobacter pylori* from gastric biopsies and antimicrobial susceptibility testing. In *Helicobacter pylori*: Techniques for Clinical Diagnosis & Basic Research (Lee A and Megraud F, Eds), WB Saunders Co. Ltd., London, pp 17-28.
22. Glupczynski Y, Broutet N, Cantagrel A, Andersen L P, Alarcon T, Lopez-Brea M, Megraud F. (2002). Comparison of the E Test and agar dilution method for antimicrobial susceptibility testing of *Helicobacter pylori*. European Journal of Clinical Microbiology and Infectious Diseases 21:549-55.
23. Glupczynski Y, Megraud F, Lopez-Brea M, Andersen L P. (2001). European multicentre survey of in vitro antimicrobial resistance in *Helicobacter pylori*. European Journal of Clinical Microbiology and Infectious Diseases 20:820-3.
24. Go M F, Smoot D T. (2000). *Helicobacter pylori*, gastric MALT lymphoma, and adenocarcinoma of the stomach. Seminars in Gastrointestinal Disease. 11:134-41.
25. Graham D Y, Lew G M, Klein P D, Evans D G, Evans D J Jr, Saeed Z A, Malaty H M. (1992). Effect of treatment of *Helicobacter pylori* infection on the recurrence of gastric ulcers or duodenal ulcer: a randomized controlled study Annals of Internal Medicine 116:705-8.
26. Hachem C Y, Clarridge J E, Reddy R, Flamm R, Evans D G, Tanaka S K, Graham D Y. (1996). Antimicrobial susceptibility testing of *Helicobacter pylori*. Comparison of E-test, broth microdilution, and disk diffusion for ampicillin, clarithromycin, and metronidazole. Diagnostic Microbiology Infectious Disease 24:37-41.
27. Haqqani M T. (2001). Acridine orange staining in the histological identification of *Helicobacter pylori*. Journal of Clinical Pathology 54:734.
28. Higuchi T, Sato Y, Murasugi S. (2001) Use of flavone derivatives for induction of beta.-lactam-sensitivity of MRSA. U.S. Pat. No. 6,294,526.
29. Hoogerwerf W A, Pasricha P J. (2001). In Goodman & Gilman's Pharmacological Basis of Therapeutics (Eds. Hardmann, J G & Limbird, L E), McGraw-Hill, pp 1005-20.
30. Iinuma M, Tsuchiya H, Sato M, Yokoyama J, Ohyama M, Tanaka T, Fujiwara S, Fujii T. (1994). Flavanones with potent antibacterial activity against methicillin-resistant *Staphylococcus aureus*. Journal of Pharmacy and Pharmacology 46:892-5.
31. Iwao E, Yamamoto K, Yokoyama Y, Hirayama F, Haga K. (2004). Potent antibacterial activity of Y-754, a novel benzimidazole compound with selective action against *Helicobacter pylori*. Journal of Infection and Chemotherapy 10:90-6.
32. Jabbar S, Khan M T H, Shahabuddin M, Choudhuri K, Sil B K. (2004). Bioactivity studies of the individual ingredients of the Dashamularishta. Pakistan Journal of Pharmaceutical Sciences 17:9-17.
33. Jayaraman K S. (2003). Technology, tradition unite in India's drug discovery scheme. Nature Medicine 9:982.
34. Khandhar M, Shah M, Santana D, Jain S. (2006). Antiulcer activity of the root bark of *Oroxylum indicum* against experimental gastric ulcers. Pharmaceutical Biology 44:363-70.
35. Kwon D H, Kim J J, Lee M, Yamaoka Y, Kato M, Osato M S, EL-Zaatari F A, Graham D Y. (2000). Isolation and characterization of tetracycline-resistant clinical isolates of *Helicobacter pylori*. Antimicrobial Agents and Chemotherapy 44: 3203-05.
36. Lee T J, Yang C L L. ((2004). Flavones as inducible nitric oxide synthase inhibitors, cyclooxygenase-2 inhibitors and potassium channel activators. U.S. Pat. No. 6,806,257.
37. Lin Y, Zembower D E, Flavin M T, Schure R, Zhao G. (2002). Biflavanoids Biflavonoids and derivatives thereof as antiviral agents. U.S. Pat. No. 6,399,654.
38. Liu L X, Durham D G, Richards R M. (2001). Vancomycin resistance reversal in enterococci by flavonoids. J of Pharmacy and Pharmacology 53:129-32.
39. Markonius M. (1995). Benzopyran phenol derivatives for use as antibacterial agents. U.S. Pat. No. 5,449,794.
40. Markonius M. (1999). Benzopyran phenol derivates for use as antibacterial, antiviral or immunostimulating agents. U.S. Pat. No. 5,861,430.

41. Mazzeo A R, Nandi J, Levine R A. (1988). Effects of ethanol on parietal cell membrane phospholipids and proton pump function. American Journal of Physiology 254:G57-64.
42. McNulty C. and PHLS *Helicobacter* Working Group: Owen R, Tompkins D, Hawtin P, McColl K, Price A, Smith G and Teare L. (2002). *Helicobacter pylori* susceptibility testing by disc diffusion. Journal of Antimicrobial Chemotherapy 49: 601-9.
43. Megraud F. (2004). Basis for the management of drug-resistant *Helicobacter pylori* infection. Drugs 64:1893-904.
44. Neeman I, Tabak M, Armon R. (1995). Therapeutic application of a thyme extract and in-vitro methods for inhibiting the growth and urease activity of *Helicobacter pylori*. U.S. Pat. No. 5,472,695.
45. Neeman I, Tabak M, Armon R. (1996). Method for inhibiting growth of *Helicobacter pylori*. U.S. Pat. No. 5,560,912.
46. Ohsaki A, Takashima J, Chiba N, Kawamura M (1999). Microanalysis of a selective potent anti-*Helicobacter pylori* compound in a Brazilian medicinal plant, *Myroxylon peruiferum* and the activity of analogues. Bioorganic and Medicinal Chemistry Letters 9:1109-12.
47. Park S, Hahm K B, Oh T Y, Jin J H, Choue R. (2004). Preventive effect of the flavonoid, wogonin, against ethanol-induced gastric mucosal damage in rats. Digestive Diseases and Science 49:384-94.
48. Rasmussen C R. (1984). N-aryl-N'-(1,4,5,6-tetrahydropyrimidin-2-yl)ureas for intestinal disorders. U.S. Pat. No. 4,466,966.
49. Ratajczyk J D, Stein R J, Swett L R. (1976). 1,3-Dimethyl-1H-pyrazolo(4,3-D) pyrimidine-7 (6H)-ones. U.S. Pat. No. 3,939,161.
50. Rao J M, Katragadda S B, Tatipaka H B, Khanapur M, Purohit M G, Pullela V S, Yadav J S. (2007). Natural agent for treatment of gastrointestinal toxicity, associated symptoms and ulcers. PCT WO/2007/080484.
51. Ray T K. (1978). Gastric $K^+$-stimulated adenosine triphosphatase. Demonstration of an endogenous activator. FEBS Letters 92: 49-52.
52. Richard M. (1972). Antibiotic production using a strain of *Aspergillus candidus*. U.S. Pat. No. 3,632,477.
53. Sanui H. (1974). Measurement of inorganic orthophosphate in biological materials: extraction properties of butyl acetate. Analytical Biochemistry 60:489-504.
54. Schiehser G A, Nielsen S T, Strike D P. (1986). N-alkylated benzo- and hetero-fused antisecretory agents. U.S. Pat. No. 4,595,757.
55. Schwan T J, Goldenberg M M. (1978). 4-Acetoxy-1,2,3,4-tetrahydro-2,2-dimethyl-6,7-methylenedioxyisoquinolinium iodide. U.S. Pat. No. 4,125,529.
56. Schwan T J, White Jr. R L. (1978). 1-(4-Chlorophenyl)-3-(1-ureido)-2-imidazolidinone. U.S. Pat. No. 4,099,009.
57. Scott M K. (1986). Furan or thiophene derivatives of iminomethyl piperidines and use to inhibit gastric secretion. U.S. Pat. No. 4,594,351.
58. Shell J W. (1996). Alkyl-substituted cellulose-based sustained-release oral drug J dosage forms. U.S. Pat. No. 5,582,837.
59. Shirai M, Kakada J, Shibata K, Morshed M, Matsushita T, Nakazawa T. (2000). Accumulation of polyphosphate granules in *Helicobacter pylori* cells under anaerobic conditions. Journal of Medical Microbiology 49:513-9.
60. Singh A B (2002). Medicinal plant survey of Dhumka, Hazaribagh and Gumla districts. Forest Resources survey Division, Ranchi.
61. Wang Y—C, Huang T-L. (2005). Anti-*Helicobacter pylori* activity of *Plumbago zeylanica* L. FEMS Immunology and Medical Microbiology 43:407-12.
62. Wermeille J, Cunninghham M, Dederding P, Girard L, Baumann R, Zelger G, Buri P, Metry J M, Sitavanc R, Gallaz L, Merki H, Godin N. (2002). Failure of *Helicobacter pylori* eradication: is poor compliance the main cause? Gastroenterologie Clinique et Biologique 26:216-9.
63. Wright G C, Goldenberg M M. (1978). O-(carboxymethyl)-4-chromanone oxime. U.S. Pat. No. 4,108,873.
64. Wu H, Shi X D, Wang H T, Liu J X. (2000). Resistance of *Helicobacter pylori* to metronidazole, tetracycline and amoxycillin. Journal of Antimicrobial Chemotherapy 46: 121-3.
65. Xu H X, Lee S F. (2001). Activity of plant flavonoids against antibiotic-resistant bacteria. Phytotherapy Research 15:39-43.
66. Xu R. (2004). Method and composition for repairing and promoting regeneration of mucosal tissue in the gastrointestinal tract. U.S. Pat. No. 6,685,971.
67. Yanai S, Sudo K, Akiyama Y, Nagahara N. (1998). Oral composition of fumagillol derivative. U.S. Pat. No. 5,846,562.
68. Yoo M, Son M W, Kim I Y, Kim W B, Kim S H, Lee S D, Lim G J, Lim J I, Ahn B O, Baik N G, Kim D S, Oh T Y, Ryu B K, Yang J S, Shin H C. (2000). Gastroprotective flavone/flavanone compounds with therapeutic effect on inflammatory bowel disease. U.S. Pat. No. 6,025,387.

Other Patent References

| | | |
|---|---|---|
| JP62145017 | June, 1987 | J P Nishino & Kobayashi |
| JP11228407 | August, 1999 | J P Higuchi & Sato |
| CN1615947 | May, 2005 | C N Zhang et al. |

Advantages

The semisynthetic molecule CPP-1 [7-O-(6-piperidin-1-yl-hexyl)-chrysin], conferred with bi-functional activity, can be prepared commercially starting from chrysin and piperidine, abundantly present in various plants (already published).

The compound is not toxic.

Peptic ulcer disease is a multietiologic disease. This designed molecule is capable of acting simultaneously against the bug *H. pylori* and the hypersecretion of gastric HCl, the two major etiologies of peptic ulcer diseases.

Unlike currently available modern medicines which require triple or quadruple therapy involving 1-2 antibiotics like clarithromycin, amoxicillin, metronidazole, one antisecretory drug like $H_2$ receptor blocker or gastric $H^+$ pump inhibitor and one mucus coating agent, the molecule CPP-1 is unique in the sense that it is strong anti *H. pylori* and also gastric antisecretory.

The most active compound CPP-1 appears to possess high therapeutic potential as it is endowed with a 6 C lipophilic spacer in its side chain which would make the compound membrane permeable.

Unlike clarithromycin which is effective only at neutral pH in eradicating *H. pylori*, the molecule CPP-1 is effective both at acidic and neutral pH.

Unlike metronidazole towards which *H. pylori* develops resistance upon long-term use, the chances of resistance development to CPP-1 is minimal.

The most active compound CPP-1 is effective even against metronidazole-resistant strains.

What is claimed is:

1. A pharmaceutical composition comprising a pharmaceutically effective amount of 5-Hydroxy-2-phenyl-7-(6-piperidin-1-yl-hexyloxy)-chromen-4-one (CPP-1); and/or 5-Hydroxy-7-[(6-(4-methyl-piperazin-1-yl)-hexyloxy]-2-phenyl-chromen-4-one (NMC-1) and/or 5-Hydroxy-2-phenyl-7-(6-morpholin-4-yl-hexyloxy)-chromen-4-one (CHM-1) and one or more pharmaceutically acceptable carriers, additives, lubricants and diluents, wherein a ratio of the compound to the carriers, additives, lubricants and diluents ranges from 1-10:10-1 w/w, for treating *Helicobacter pylori* infection and gastric hypersecretion in a subject.

2. The composition of claim 1, wherein the one or more pharmaceutically acceptable carriers used are selected from the group consisting of proteins, carbohydrates, sugar, magnesium stearate, cellulose, calcium carbonate, starch-gelatin paste and pharmaceutically acceptable excipients, diluents and solvents.

3. The composition of claim 1, wherein the composition is administered in a human at a dose ranging between 20-60 mg twice per day.

4. The composition of claim 1, wherein the composition is used for treating or preventing *Helicobacter pylori* infection and gastric hypersecretion leading to management of peptic ulcer diseases, which include one or more of the following disorders: gastric peptic ulcer, duodenal peptic ulcer, chronic and acute gastritis, chronic and acute duodenitis, non-ulcer dyspepsia, gastro esophageal reflux disorders, mucosa-associated lymphoid tissue lymphoma and gastric adenocarcinoma.

* * * * *